US007666422B2

(12) United States Patent
Siegall et al.

(10) Patent No.: US 7,666,422 B2
(45) Date of Patent: *Feb. 23, 2010

(54) METHODS FOR THE TREATMENT OF CANCER USING ANTI-CD40 ANTIBODIES

(75) Inventors: Clay B. Siegall, Bothell, WA (US); Alan F. Wahl, Mercer Island, WA (US); Joseph A. Francisco, Edmonds, WA (US); Henry Perry Fell, Jr., Redmond, WA (US)

(73) Assignee: Seattle Genetics, Inc., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/356,511

(22) Filed: Jan. 20, 2009

(65) Prior Publication Data

US 2009/0280117 A1    Nov. 12, 2009

Related U.S. Application Data

(62) Division of application No. 10/846,981, filed on May 14, 2004, now Pat. No. 7,498,032, which is a division of application No. 09/724,530, filed on Nov. 28, 2000, now Pat. No. 6,843,989, which is a division of application No. 09/328,296, filed on Jun. 8, 1999, now Pat. No. 6,946,129.

(51) Int. Cl.
*A61K 39/395* (2006.01)
*C07K 16/28* (2006.01)

(52) U.S. Cl. ............... 424/153.1; 424/130.1; 424/133.1; 424/141.1; 424/143.1; 424/144.1; 424/152.1; 424/173.1; 530/387.1; 530/387.3; 530/388.1; 530/388.2; 530/388.22; 530/388.7; 530/388.73

(58) Field of Classification Search ....................... None
See application file for complete search history.

(56) References Cited

U.S. PATENT DOCUMENTS

| | | | |
|---|---|---|---|
| 5,182,368 A | 1/1993 | Ledbetter et al. |
| 5,354,847 A | 10/1994 | Liu et al. |
| 5,530,101 A | 6/1996 | Queen et al. |
| 5,540,926 A | 7/1996 | Aruffo et al. |
| 5,545,806 A | 8/1996 | Lonberg et al. |
| 5,597,569 A | 1/1997 | Siegall et al. |
| 5,674,492 A | 10/1997 | Armitage et al. |
| 5,677,165 A | 10/1997 | De Boer et al. |
| 5,801,227 A | 9/1998 | Fanslow et al. |
| 5,872,215 A | 2/1999 | Osbourne et al. |
| 5,874,082 A | 2/1999 | De Boer |
| 5,985,847 A | 11/1999 | Carson et al. |
| 6,037,454 A | 3/2000 | Jardieu et al. |
| 6,051,228 A | 4/2000 | Aruffo et al. |
| 6,054,297 A | 4/2000 | Carter et al. |
| 6,056,959 A | 5/2000 | De Boer et al. |
| 6,838,261 B1 | 1/2005 | Siegall et al. |
| 6,843,989 B1 | 1/2005 | Siegall et al. |
| 6,946,129 B1 | 9/2005 | Siegall et al. |
| 7,498,032 B2 | 3/2009 | Siegall et al. |
| 7,507,414 B2 | 3/2009 | Rosen et al. |
| 7,510,711 B2 | 3/2009 | Siegall et al. |
| 7,563,445 B2 | 7/2009 | Melief |
| 2003/0022860 A1 | 1/2003 | Melief et al. |
| 2005/0008637 A1 | 1/2005 | Siegall et al. |
| 2006/0074008 A1 | 4/2006 | Senter |

FOREIGN PATENT DOCUMENTS

| | | |
|---|---|---|
| WO | WO 94/04570 A1 | 3/1994 |
| WO | WO 95/17202 A1 | 6/1995 |
| WO | WO 96/18413 A1 | 6/1996 |
| WO | WO 97/31025 A1 | 8/1997 |
| WO | WO 98/33810 A2 | 8/1998 |
| WO | WO 98/58678 A1 | 12/1998 |
| WO | WO 99/42075 A2 | 8/1999 |
| WO | WO 00/75348 A1 | 12/2000 |
| WO | WO 2006/128103 A2 | 11/2006 |
| WO | WO 2007/075326 A2 | 7/2007 |

OTHER PUBLICATIONS

Bridges et al., "Selective In Vivo Antitumor Effects of Monoclonal Anti-I-A Antibody on a B Cell Lymphoma," J. Immunol., 1987, 139(12),4242-4249.
Carter et al., "Humanization of an anti-p185HER2 antibody for human cancer therapy," Proc. Natl. Acad. Sci. USA, 1992, 89, 4285-4289.
Cunningham et al., "Receptor and Antibody Epitopes in Human Growth Hormone Identified by Homolog-Scanning Mutagenesis," Science, 1989, 243, 1330-1336.
U.S. Appl. No. 11/913,305, filed May 26, 2005, Presta et al.
U.S. Appl. No. 12/302,743, filed May 7, 2009, Siegall et al.
U.S. Appl. No. 12/390,170, filed Feb. 20, 2009, Siegall et al.
Paulie et al., "Monoclonal antibodies to antigens associated with transitional cell carcinoma of the human urinary bladder," *Cancer Immunol. Immunother.*, 1984, 17, 173-179.
Pellat-Decounynck et al., "Expression of CD28 and CD40 in Human Myeloma Cells: A Comparative Study with Normal Plasma Cells," *Blood*, 1994, 84(8), 2597-2603.
www.ncbi.nlm.nih.gov (National Center for Biotechnology Information) GenBank Accession No. A61522, Oct. 15, 1994, 7.5k surfactant-associated protein—human (fragment).
www.ncbi.nlm.nih.gov (National Center for Biotechnology Information) GenBank Protein Accession No. S69899, 1997, Ig heavy chain V region (clone RFTS7H), rheumatoid factor—human.

(Continued)

*Primary Examiner*—Phillip Gambel
(74) *Attorney, Agent, or Firm*—Townsend and Townsend and Crew, LLP

(57) ABSTRACT

The present invention relates to methods and compositions for the prevention and treatment of cancer, inflammatory diseases and disorders or deficiencies of the immune system. The methods of the invention comprise administering a CD40 binding protein that potentiates the binding of CD40 to CD40 ligand.

17 Claims, 10 Drawing Sheets

Figure 4:
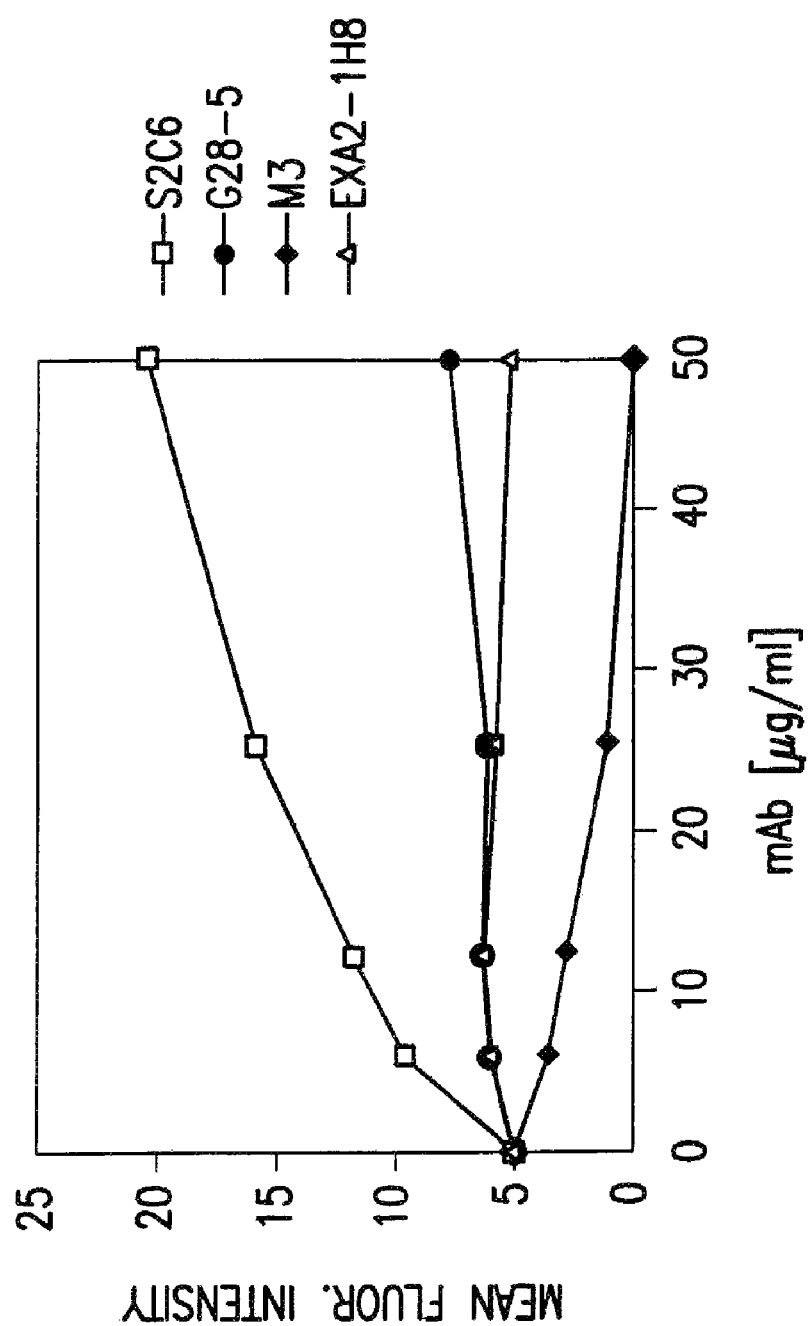

OTHER PUBLICATIONS www.ncbi.nlm.nih.gov (National Center for Biotechnology Information) GenBank Accession No. D50136, Apr. 12, 1995, Mus musculus mRNA for anti-acid phosphatase variable light chain 11, partial cds.

www.ncbi.nlm.nih.gov (National Center for Biotechnology Information) GenBank Protein Accession No. C29380, 1988, Ig kappa chain precursor V region (BC-1004)—mouse (fragment).

www.ncbi.nlm.nih.gov (National Center for Biotechnology Information) GenBank Protein Accession No. S67941, 1997, Ig heavy chain variable region, subgroup I (clone MH52)—human (fragment).

Accession No. W78434, 1998, Antibody light chain directed to HER3 clone 18.

Accession No. Y06716, 1999, Antibody 12B5 single chain Fv (scFv) fragment.

Ada, G., "The coming of age of immunotherapy," Immunology and Cell Biology, 1999, 77, p. 180-185.

Alessandrini, A. et al., "Coordination of immunoglobulin DJH transcription and D-to-JH rearrangement by promoter-enhancer approximation," Mol. Cell Biol., 1991, 11(4), 2096-2107.

Andersen et al., "Soluble CD40 ligand induces cell cycle progression in primary mantle cell lymphoma," Blood, 1999, 94(10), Suppl. 1, p. 630a.

Apostolopoulos et al., "MUC1 cross-reactive Gala(1,3)Gal antibodies in humans switch immune response from cellular to humoral," Nature Medicine, 1998, 4, 315-320.

Armitage et al., "Distinct patterns of inhibition by CD40 mAb of the CD40 ligand-CD40 interaction," Leukocyte Typing V, Schlossman et al. (eds.), 1995, 1, 551-552.

Becker et al., "Tumor escape mechanisms from immunosurveillance: induction of unresponsiveness in a specific MHC-restricted CD4+ human T cell clone by the autologous MHC class II+ melanoma," International Immunology, 1993, 5(12), 1501-1508.

Bender et al., Human antibodies and Hybridomas, 1993, 4, 74-79 (Abstract).

Bendig, Methods: A Companion to Methods in Enzymology. 8:83-93, 1995.

Bjorck et al., "Antibodies to distinct epitopes on the CD40 molecule co-operate in stimulation and can be used for the detection of soluble CD40," Immunology, 1994, 83, 430-437.

Bjorck, P. et al., "CD40 antibodies defining distinct epitopes display qualitative differences in their induction of B-cell differentiation," Immunology, 1996, 87(2), 291-295.

Braesch-Andersen et al., Isolation and characterization of two bladder carcinoma-associated antigens. J. Immunol Methods. Nov. 20, 1986;94(1-2):145-151b.

Bubenik, J. et al., "Monoclonal antibodies against human urinary bladder carcinomas: selectivity and utilization for gamma scintigraphy," Eur. J. Cancer Clin.Oncol., 1985, 21(6), 701-710.

Buchsbaum et al., "Improved Delivery of Radiolabeled Anti-B1 Monoclonal Antibody to Raji Lymphoma Xenografts by Predosing with Unlabeled Anti-B1 Monoclonal Antibody," Cacner Research, 1992, 52, 637-642.

Buhmann et al., "CD40-Activated B-cell Chronic Lymphocytic Leukemia Cells for Tumor Immunotherapy: Stimulation of Allogeneic Versus Autologous T Cells Generates Different Types of Effector Cells," Blood, 1999, 93, p. 1992-2002.

Cattan et al., "The C.B. 17 SCID Mouse Strain as a Model for Human Disseminated Leukemia and Myeloma In Vivo," Leukemia Research, 1994, 18(7), 513-522.

Caux et al., "Activation of Human Dendritic Cells through CD40 Cross-Linking," Journal of Experimental Medicine, 1994, 180, p. 1263-1272.

Cella et al., "Ligation of CD40 on Dendritic Cells Triggers Production of High Levels of Interleukin-12 and Enhances T Cell Stimulatory Capacity: T-T Help via APC Activation," Journal of Experimental Medicine, 1996, 184, p. 747-752.

Challa, A. et al., "Epitope-dependent synergism and antagonism between CD40 antibodies and soluble CD40 ligand for the regulation of CD23 expression and IgE synthesis in human B cells," Allergy, 1999, 54(6), 576-583.

Charreau et al., "Transgenesis in rats: technical aspects and models", Transgenic Res. Jul. 1996;5(4):223-234 (Abstract).

Chen et al., "Nucleotide and translated amino acid sequences of cDNA coding for the variable regions of the light and heavy chains of mouse hybridoma antibodies to blood group A and B substances," J. Biol. Chem., 1987, 262(28), 13579-13583.

Chen et al., "Enhancement And Destruction Of Antibody Function By Somatic Mutation; Unequal Occurrence is Controlled by V Gene Combinational Associations," EMBO J., 14: 2784-2794, 1995.

Clark, E.A. et al., "Activation of human B cells mediated through two distinct cell surface differentiation antigens, Bp35 and Bp50," PNAS U.S.A., 1986, 83(12), 4494-4498.

Clark, (ed.), "Protein Engineering of Antibody Molecules for Prophylactic and Therapeutic Application in Man", 1993. The Alden Press, pp. 4-5.

Colman, "Effects Of Amino Acid Sequence Changes on /Antibody-Antigen Interactions," Research in Immunology 145: 33-36, 1994.

Costello et al., "Tumor Escape from Immune Surveillance," Archivum Immunologiae et Therapiae Expereimentalis, 1999, 47, p. 83-88.

De Paoli, P., "High CD40 membrane expression in AIDS-related lymphoma B cell lines is associated with the CD45RA+, CD45RO+, CD95+ phenotype and high levels of its soluble form in culture supernatants," Cytometry, 1997, 30(1), 33-38.

Fanslow et al., "CD40 mAb M2 and M3 inhibit CD40 ligand binding and function," Leukocyte Typing V 1995, Schlossman et al. (eds.), 1, 555-556.

Francisco et al., "Agonistic Properties and in Vivo Antitumor Activity of the Anti-CD40 Anitbody SGN-14", Cancer Research 60:3225-3231, 2000.

Francisco, JA et al., "Construction, expression, and characterization of BD1-G28-5 sFv, a single-chain anti-CD40 immunotoxin containing the ribosome-inactivating protein bryodin 1," J. Biol. Chem., 1997, 272(39), 24165-24169.

Frisch et al., "A Soluble Immunogolobulin Variable Domain without a Disulfide Bridge," Biol. Chem., 1994, Hoppe-Seyler, 375, 353-356.

Funakoshi, S. et al., "Differential in vitro and in vivo antitumor effects mediated by anti-CD40 and anti-CD20 monoclonal antibodies against human B-cell lymphomas," J. Immunother Emphasis Tumor Immunol., 1996, 19(2), 93-101.

Funakoshi, S. et al., "Inhibition of human B-cell lymphoma growth by CD40 simulation", Blood, 1994, 83(10), 2787-94.

Ghetie et al., "Disseminated or Localized Growth of a Human B-Cell Tumor (Daudi) in SCID Mice," Int. J. Cancer, 1990, 45, p. 481-485.

Gilliland, L.K. et al., "Rapid and reliable cloning of antibody variable regions and generation of recombinant single chain antibody fragments," Tissue Antigens, 1996, 47(1), 1-20.

Grafton, G. et al., "Mechanisms of antigen receptor-dependent apoptosis of human B lymphoma cells probed with a panel of 27 monoclonal antibodies," Cell Immunol., 1997, 182(1), 45-56.

Greenwood and Clark, "Effector functions of matched sets of recombinant human IgG subclass antibodies," Protein Engineering of Antibody Molecules for Prophylactic and Therapeutic Applications in Man., Clark (ed.), 1993, 85-87.

Greenwood et al., "Effector functions of matched sets of recombinant human IgG subclass antibodies," Protein Engineering of Antibody Molecules for Prophylactic and Therapeutic Applications in Man., Clark (ed.), 1993, 85-100.

Grewal, IS et al., "CD40 and CD154 in cell-mediated immunity," Annu. Rev. Immunol., 1998, 16, 111-135.

Gura, "Systems For Identifying New Drugs Are Often Faulty," Science, 1997, 278, 1041-2.

Henriquez et al., "Differential Response to CD40 Litigation Among Burkitt Lymphoma Lines That Are Uniformly Responsive to Epstein-barr Virus Latent Membrane Protein 11," Journal of Immunology, 1999, 162, 3298-3307.

Herbert et al., "Inhibition of specific antibody production by CD40L and a panel of antibodies to CD40," Leukocyte Typing V, 1995, Schlossman et al. (eds.), 1, 552-554.

Hiraki et al., "Loss of HLA Haplotype in Lung Cancer Cell Lines: Implications for Immunosuveillance of Altered HLA Class I/II Phenotypes in Cancer," Clinical Cancer Research, 1999, 5, 933-936.

Hirano et al., "Inhibition of Human Breast Carcinoma Growth by a Soluble Recombinant Human CD40 Ligand," Blood, 1999, 93(9), 2999-3007.

Kaminski et al., "Pivotal Study of Iodine 1 131 Tositumomab for Chemotherapy-Refractory Low-Grade of Transformed Low-Grade B-Cell Non-Hodgkin's Lymphomas," J. of Clinical Oncology, 2001, 19(19), 3918-3928.

Katira et al., "CD40 Workshop Panel report," Leukocyte Typing V, 1995, Schlossman et al. (eds.), 547-550.

Katira et al., "Identification of co-operative epitopes on CD40 supports the existence of a second CD40 ligand," Leukocyte Typing V, 1995, Schlossman et al. (eds.), 1, 554.

Kawabe et al., "Generation and characterization of CD40-deficient mice," Leukocyte Typing V, 1995, Schlossman et al. (eds.), 1, 550-551.

Kawaguchi et al., Proc. Ann. Meet. Am. Assoc. Cancer Res., 1997, 38, p. A2319 (Abstract).

Kawata et al., "Establishment of New SCID and Nude Mouse Models of Human B-Leukemia/Lymphoma and Effective Therapy of the Tumors with Immunotoxin and Monoclonal Antibody: Marked Difference between the SCID and Nude Mouse Models in the Antitumor Efficacy of Monoclonal Antibody," *Cancer Research*, 1994, 54, 2688-2694.

Kehry, MR, "CD40-mediated signaling in B cells, Balancing cell survival, growth, and death," *J. Immunol.*, 1996, 156(7), 2345-2348.

Kim et al., "Restoring allosterism with compensatory mutations in hemogloblin," *PNAS*, 1994, 91, 11547-11551.

Koho, H. et al., "Monoclonal antibodies to antigens associated with transitional cell carcinoma of the human urinary bladder," *Cancer Immunol. Immunother.*, 1984, 17, 165-172.

Kuhne, M.R. et al., "Assembly and regulation of the CD40 receptor complex in human B cells," *J. Exp. Med.*, 1997, 186(2), 337-342.

Kussie, et al., "A Single Engineered Amino Acid Substitution Changes Antibody Fine Specificity," *J. Immunol.*, 152: 146-152, 1994.

Kwekkeboom et al., "Helper effector function of human T cells stimulated by anti-CD3 mAb can be enhanced by co-stimulatory signals and is partially dependent on CD40-CD40- ligand interaction," Immunology, 1994, *Eur. J. Immunol.* 24:508-517.

Kwekkeboom et al., "CD40 plays an essential role in the activation of human B cells by murine EL4B5," *Immunology*, 1993, 79, 439-444.

Ledbetter et al., "Augmentation of normal and malignant B Cell Proliferation by Monoclonal antibody to the b cell-specific antigen BP50 (CDW40)[1]," *J. Immunol.*, 1987, 138(3), 788-794.

Lund et al., "Multiple Interactions Of IgG With Its Core Oligosaccharide Can Modulate Recognition By Complement And Human Fcγ Receptor I And Influence The Synthesis Of Its Oligosaccharide Chains," *The Journal of Immunology* 157: 4963-4969, 1996.

Machaty et al., "The use of nuclear transfer to produce transgenic pigs", *Cloning Stem Cells*. 2002:4(1):21-27 (Abstract).

Malik, N. et al., "Activation of human monocytes through CD40 indices matrix metalloproteinases," *J. Immunol.*, 1996, 156(10), 3952-3960.

Matsui et al., "A model for CD+8 CTL tumor immunosurveillance and regulation of tumor escape by CD+4 cells," *J. Immunology*, 1999, 163, p. 184-193.

Matthews, B., "Genetic and Structural Analysis of the Protein Stability Problem," *Perspectives in Biochemistry*, 1989, 2, 6-9.

Matthews and Van Holde, *Biochemistry* (textbook), 2nd edition, pp. 165-171.

Murphy, WJ et al., "Antibodies to CD40 prevent Epstein-Barr virus-mediated human B-cell lymphomagenesis in severe combined immune deficient mice given human perlpheral blood lymphocytes," *Blood*, 1995, 86(5), 1946-1953.

Nancarrow et al., *Methods in Molecular Biology*, 1993, 18:273-303 (Abstract).

Noelle, RJ et al., "A 39-kDa protein on activated helper T cells binds CD40 and transduces the signal for cognate activation of B cells," *PNAS U.S.A.*, 1992, 89(14), 6550-6554.

Ostrowski et al., "Inhibition of Angiogenesis in the Treatment of Tumors," *Archivum Immunologiae et Therapiae Experimentalis*, 2001, 49, 27-31.

Paulie et al., "The Human B Lymphocyte and Carcinoma Antigen, CDw40, Is A Phosphoprotein Involved in Growth Signal Transduction," *J. Immunol.*, 1989, 142(2), 590-595.

Pound, JD et al., "Minimal cross-linking and epitope requirements for CD40-dependent suppression of apoptosis contrast with those for promotion of the cell cycle and homotypic adhesions in human B cells," *Int. Immunol.*, 1999, 11(1), 11-20.

Riechmann et al., "Reshaping human antibodies for therapy," *Nature*, 1988, 332, 323-327.

Rudikoff et al., "Single Amino Acid Substitution Altering Antigen-Binding Specificity," *Proc Natl Acad Sci USA* 79: 1979-1983, 1982.

Schlom, Jeffery, "Monoclonal Antibodies: They're More and Less Than You Think," *Molecular Foundation of Oncology*, Broader, S. (ed.), 1991, 95-134.

Schultze et al., *Blood*, 1996, 88(10), Suppl. 1, part 1-2, p. 162A (Abstract).

Schultze, J.L., "T-Cell-Mediated Immunity against B-Cell Malignancies: Preclinical Results and Translation into a Novel Immunotherapeutic Approach for B-Cell Malignancies," *Haematology and Blood Transfusion*, 1998, 39, 716-731.

Sotomayor et al., *Blood*, 1998, 92(10). Suppl. 1, part 1-2, p. 541A.

Speiser, DE et al., "A regulatory role for TRAF1 in antigen-induced apoptosis of T cells," *J Exp. Med.*, 1997, 185(10), 1777-1783.

Stamenkovic, I. et al., "A B-lymphocyte activation molecule related to the nerve growth factor receptor and induced by cytokines in carcinomas," *EMBO J.*, 1989 8(5), 1403-1410.

Tillman et al., "Both IgM and IgG Anti-DNA Antibodies Are the Products of Clonally Selective B Cell Stimulation in (NZB×NZW)F1 Mice," *J. Exp. Med.*, 1992, 176(3), 761-779.

Tutt, AL et al., "Monoclonal Antibody Therapy of B cell Lymphoma: Signaling Activity on Tumor Cells Appears More Important Than Recruitment of Effectors," *J. Immunol.*, 1998, 161(6), 3176-3185.

Uckun et al., "Temporal association of CD40 antigen expression with discreet stages of human B-cell ontogeny and the efficacy of the anti-CD40 immunotoxins," *Blood*, 1990, 76 2449-2456 (abstract only).

Van Kooten, C. et al., "Functions of CD40 on B cells, dendritic cells and other cells," *Curr. Opin. Immunol.*, 1997, 9(3), 330-337.

Vonderheide et al., "CD40 ligation of solid tumors does not induce the surgace phenotype characteristic of professional antigen presenting cells," *Proceed. Amer. Assoc. Cancer Research*, 1999, 40, p. 472.

Yeh, W.C. et al., "Early Lethality Functional Nf-kB Activation, and Increased Sensitivity to TNF-Induced Cell Death in TRAF2-Deficient Mice," *Immunity*, 1997, 7, 715-725.

Younes, A et al., "Elevated levels of biologically active soluble CD40 ligand in the serum of patients with chronic lymphocytic leukaemia," *Br. J. Haematology*, 1998, 100, 135-141.

EP 00939679.7, Supplementary Partial European Search Report mailed Apr. 18, 2005.

EP 06771453.5 Supplementary Partial European Search Report mailed Mar. 25, 2009.

PCT/US2000/015749 (published as WO/2000/075348 A1), International Search Report mailed on Sep. 7, 2000.

International Search Report for PCT/US2006/020688 (published as WO/2006/128103 A3) mailed on Nov. 30, 2006.

International Search Report for PCT/US2006/047308 (published as WO/2007/075326 A3) mailed Jun. 12, 2008.

Hollingsworth, "Seattle Genetics: SGN40 Still Alive After Lymphoma Bust", *BioWorld Today* 20(192): 1, 4 (Oct. 6, 2009).

Seattle Genetics News Release: "Seattle Genetics Announces Discontinuation of Dacetuzumab Phase IIb Diffuse Large B-Cell Lymphoma Clinical Trial", Oct. 5, 2009.

```
GATGTTGTGATGACCCAAACTCCACTCTCTCCCTGCCTGTCAGTCTTGGAGCTCAAGCCTCCATCTCTTGCAGATCT
----:----|----:----|----:----|----:----|----:----|----:----|----:----|----:----
CTACAACACTACTGGGTTTGAGGTGAGAGGGACGGACAGTCAGAGTCGAGAACCTCGAGTTCGGAGGTAGAGAACGTCTAGA
 D  V  V  M  T  Q  T  P  L  S  L  P  V  S  L  G  A  Q  A  S  I  S  C  R  S                        75

AGTCAGAGCCTTGTACACAGTAATGGAAACACCTTTTACATTGGTACCTGAGAAGCCAGGCCAGTCTCCAAAA
----:----|----:----|----:----|----:----|----:----|----:----|----:----|----:----
TCAGTCTCGGAACATGTGTCATTACCTTTGTGGAAAATGTAACCATGGACGTCTTCGGTCCGGTCAGAGGTTTT
 S  Q  S  L  V  H  S  H  G  H  T  F  L  H  V  Y  L  Q  K  P  G  Q  S  P  K                       150

CTCCTGATCTACACAGTTTCCAACCGATTTTCTGGGGTCCCAGACAGGTTCAGTGGCAGTGGATCAGGGACAGAT
----:----|----:----|----:----|----:----|----:----|----:----|----:----|----:----
GAGGACTAGATGTGTCAAAGGTTGGCTAAAAGACCCCAGGGTCTGTCCAAGTCACCGTCACCTAGTCCCTGTCTA
 L  L  I  Y  T  V  S  H  R  F  S  G  V  P  D  R  F  S  G  S  G  S  G  T  D                       225

TTCACACTCAAGATCAGCAGAGTGGAGGCTGAGGATCTGGGAGTTTATTTCTGCTCTCAAACTACACATGTTCCG
----:----|----:----|----:----|----:----|----:----|----:----|----:----|----:----
AAGTGTGAGTTCTAGTCGTCTCACCTCCGACTCCTAGACCCTCAAATAAAGACGAGAGTTTGATGTGTACAAGGC
 F  T  L  K  I  S  R  V  E  A  E  D  L  G  V  Y  F  C  S  Q  T  T  H  V  P                       300

TGGACGTTCGGTGGAGGCACCAAGCTGGAAATCCAA
----:----|----:----|----:----|----:--    336
ACCTGCAAGCCACCTCCGTGGTTCGACCTTTAGGTT
 W  T  F  G  G  G  T  K  L  E  I  Q
```

FIG.1

```
GAGGTCCAGCTGCAGCAGTCTGGACCTGACCTGGTGAAGCCTGGGGCTTCAGTGAAGATCTCCTGCAAGGCTTCT
----|----|----|----|----|----|----|----|----|----|----|----|----|----|----|   75
CTCCAGGTCGACGTCGTCAGACCTGGACTCGGACCACTTCGGACCCCGAAGTCACTTCTAGAGGACGTTCCGAAGA
 E  V  Q  L  Q  Q  S  G  P  D  L  V  K  P  G  A  S  V  K  I  S  C  K  A  S

GGTTACTCATTCACTGGCTACTACATACACTGGGTGAAGCAGAGCCATGGAAAGAGCCTTGAGTGGATTGGACGT
----|----|----|----|----|----|----|----|----|----|----|----|----|----|----|   150
CCAATGAGTAAGTGACCGATGATGTATGTGACCCACTTCGTCTCGGTACCTTTCTCGGAACTCACTCCTAACCTGCA
 G  Y  S  F  T  G  Y  Y  I  H  V  V  K  Q  S  H  G  K  S  L  E  V  I  G  R

GTTATTCCTAACAATGGAGGCACTAGTTACAACCAGAAGTTCAAGGGCAAGGCCATATTAACTGTAGACAAGTCA
----|----|----|----|----|----|----|----|----|----|----|----|----|----|----|   225
CAATAAGGATTGTTACCTCCGTGATCAAGTTCCCGTTCCAAGTTCCGTTCCGGTATAATTGACATCTGTTCAGT
 V  I  P  H  H  G  G  T  S  Y  H  Q  K  F  K  G  K  A  I  L  T  V  D  K  S

TCCAGCACAGCCTACATGGAACTCCGCAGCCTGACATCTGAGGACTCTGCGGTCTATTACTGTGCAAGAGAAGGG
----|----|----|----|----|----|----|----|----|----|----|----|----|----|----|   300
AGGTCGTGTCGGATGTACCTTGAGGCGTCGGACTGTAGACTCCTGAGACGCCAGATAATGAGACGTTCTCTTCCC
 S  S  T  A  Y  M  E  L  R  S  L  T  S  E  D  S  A  V  Y  Y  C  A  R  E  G

ATCTACTGGGGCCACGGCACCACTCTCACAGTCTCCTCA
----|----|----|----|--    342
TAGATGACCCCGGTGCCGTGGTGAGAGTGTCAGAGGAGT
 I  Y  W  G  H  G  T  T  L  T  V  S  S
```

FIG.2

S2C6 VL

DVVVTQTPLSLPVSLGAQASISCRSSQSLVHSNGNTFLHWYLQKPGQSPKL
                              CDR1

LIYTVSNRFSGVPDRFSGSGSGTDFTLKISRVEAEDLGVYFCSQTTHVPWT
  CDR2                                        CDR3

FGGGTKLEIQ

FIG. 3A

S2C6 VH

EVQLQQSGPDLVKPGASVKISCKASGYSFTGYYIHWVKQSKGHSLEWIGRV
                         CDR1

IPNNGGTSYNQKFKGKAILTVDKSSSTAYMELRSLTSEDSAVYYCAREGIY
  CDR2                                        CDR3

WWGHGTTLTVSS

FIG. 3B

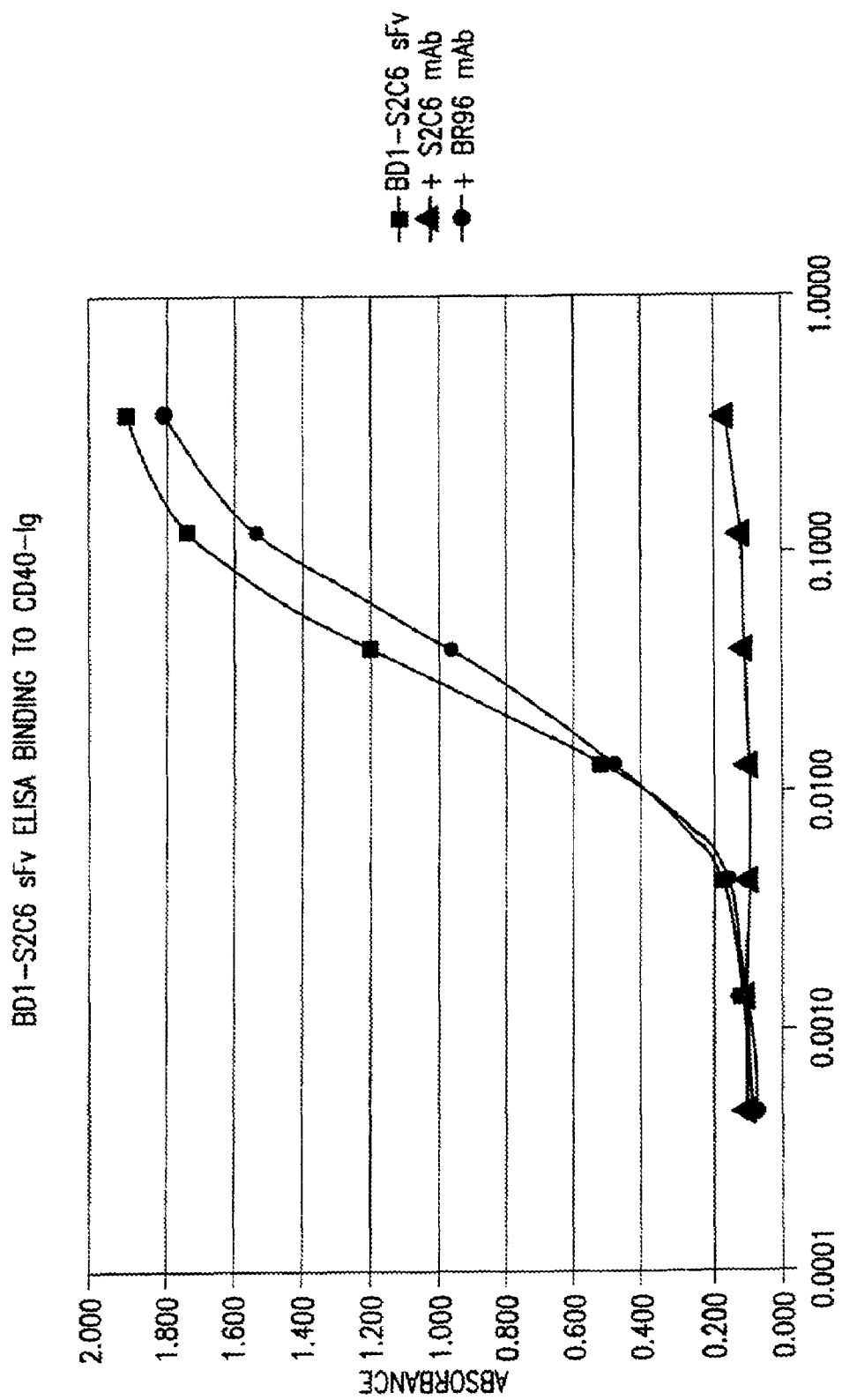

SEQUENCE LISTING

```
<160> NUMBER OF SEQ ID NOS: 15

<210> SEQ ID NO 1
<211> LENGTH: 336
<212> TYPE: DNA
<213> ORGANISM: Mus musculus
<220> FEATURE:
<221> NAME/KEY: CDS
<222> LOCATION: (1)..(336)

<400> SEQUENCE: 1 gat gtt gtg gtg acc caa act cca ctc tcc ctg cct gtc agt ctt gga      48
Asp Val Val Val Thr Gln Thr Pro Leu Ser Leu Pro Val Ser Leu Gly
 1               5                  10                  15 gct caa gcc tcc atc tct tgc aga tct agt cag agc ctt gta cac agt      96
Ala Gln Ala Ser Ile Ser Cys Arg Ser Ser Gln Ser Leu Val His Ser
             20                  25                  30 aat gga aac acc ttt tta cat tgg tac ctg cag aag cca ggc cag tct     144
Asn Gly Asn Thr Phe Leu His Trp Tyr Leu Gln Lys Pro Gly Gln Ser
         35                  40                  45 cca aaa ctc ctg atc tac aca gtt tcc aac cga ttt tct ggg gtc cca     192
Pro Lys Leu Leu Ile Tyr Thr Val Ser Asn Arg Phe Ser Gly Val Pro
     50                  55                  60 gac agg ttc agt ggc agt gga tca ggg aca gat ttc aca ctc aag atc     240
Asp Arg Phe Ser Gly Ser Gly Ser Gly Thr Asp Phe Thr Leu Lys Ile
 65                  70                  75                  80 agc aga gtg gag gct gag gat ctg gga gtt tat ttc tgc tct caa act     288
Ser Arg Val Glu Ala Glu Asp Leu Gly Val Tyr Phe Cys Ser Gln Thr
                 85                  90                  95 aca cat gtt ccg tgg acg ttc ggt gga ggc acc aag ctg gaa atc caa     336
Thr His Val Pro Trp Thr Phe Gly Gly Gly Thr Lys Leu Glu Ile Gln
            100                 105                 110

<210> SEQ ID NO 2
<211> LENGTH: 112
<212> TYPE: PRT
<213> ORGANISM: Mus musculus

<400> SEQUENCE: 2
```

```
Asp Val Val Thr Gln Thr Pro Leu Ser Leu Pro Val Ser Leu Gly
 1               5                  10                  15

Ala Gln Ala Ser Ile Ser Cys Arg Ser Ser Gln Ser Leu Val His Ser
             20                  25                  30

Asn Gly Asn Thr Phe Leu His Trp Tyr Leu Gln Lys Pro Gly Gln Ser
         35                  40                  45

Pro Lys Leu Leu Ile Tyr Thr Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Thr
                 85                  90                  95

Thr His Val Pro Trp Thr Phe Gly Gly Gly Thr Lys Leu Glu Ile Gln
             100                 105                 110
```

<210> SEQ ID NO 3
<211> LENGTH: 16
<212> TYPE: PRT
<213> ORGANISM: Mus musculus

<400> SEQUENCE: 3

```
Arg Ser Ser Gln Ser Leu Val His Ser Asn Gly Asn Thr Phe Leu His
 1               5                  10                  15
```

<210> SEQ ID NO 4
<211> LENGTH: 7
<212> TYPE: PRT
<213> ORGANISM: Mus musculus

<400> SEQUENCE: 4

```
Thr Val Ser Asn Arg Phe Ser
 1               5
```

<210> SEQ ID NO 5
<211> LENGTH: 9
<212> TYPE: PRT
<213> ORGANISM: Mus musculus

<400> SEQUENCE: 5

```
Ser Gln Thr Thr His Val Pro Trp Thr
 1               5
```

<210> SEQ ID NO 6
<211> LENGTH: 342
<212> TYPE: DNA
<213> ORGANISM: Mus musculus
<220> FEATURE:
<221> NAME/KEY: CDS
<222> LOCATION: (1)..(342)

<400> SEQUENCE: 6

```
gag gtc cag ctg cag cag tct gga cct gac ctg gtg aag cct ggg gct      48
Glu Val Gln Leu Gln Gln Ser Gly Pro Asp Leu Val Lys Pro Gly Ala
 1               5                  10                  15 tca gtg aag atc tcc tgc aag gct tct ggt tac tca ttc act ggc tac      96
Ser Val Lys Ile Ser Cys Lys Ala Ser Gly Tyr Ser Phe Thr Gly Tyr
             20                  25                  30 tac ata cac tgg gtg aag cag agc cat gga aag agc ctt gag tgg att     144
Tyr Ile His Trp Val Lys Gln Ser His Gly Lys Ser Leu Glu Trp Ile
         35                  40                  45 gga cgt gtt att cct aac aat gga ggc act agt tac aac cag aag ttc     192
```

```
Gly Arg Val Ile Pro Asn Asn Gly Gly Thr Ser Tyr Asn Gln Lys Phe
 50                  55                  60 aag ggc aag gcc ata tta act gta gac aag tca tcc agc aca gcc tac       240
Lys Gly Lys Ala Ile Leu Thr Val Asp Lys Ser Ser Ser Thr Ala Tyr
 65                  70                  75                  80 atg gaa ctc cgc agc ctg aca tct gag gac tct gcg gtc tat tac tgt       288
Met Glu Leu Arg Ser Leu Thr Ser Glu Asp Ser Ala Val Tyr Tyr Cys
                 85                  90                  95 gca aga gaa ggg atc tac tgg tgg ggc cac ggc acc act ctc aca gtc       336
Ala Arg Glu Gly Ile Tyr Trp Trp Gly His Gly Thr Thr Leu Thr Val
             100                 105                 110 tcc tca                                                                342
Ser Ser <210> SEQ ID NO 7
<211> LENGTH: 114
<212> TYPE: PRT
<213> ORGANISM: Mus musculus

<400> SEQUENCE: 7

Glu Val Gln Leu Gln Gln Ser Gly Pro Asp Leu Val Lys Pro Gly Ala
 1               5                  10                  15

Ser Val Lys Ile Ser Cys Lys Ala Ser Gly Tyr Ser Phe Thr Gly Tyr
             20                  25                  30

Tyr Ile His Trp Val Lys Gln Ser His Gly Lys Ser Leu Glu Trp Ile
         35                  40                  45

Gly Arg Val Ile Pro Asn Asn Gly Gly Thr Ser Tyr Asn Gln Lys Phe
     50                  55                  60

Lys Gly Lys Ala Ile Leu Thr Val Asp Lys Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Glu Gly Ile Tyr Trp Trp Gly His Gly Thr Thr Leu Thr Val
             100                 105                 110

Ser Ser

<210> SEQ ID NO 8
<211> LENGTH: 6
<212> TYPE: PRT
<213> ORGANISM: Mus musculus

<400> SEQUENCE: 8

Thr Gly Tyr Tyr Ile His
 1               5

<210> SEQ ID NO 9
<211> LENGTH: 17
<212> TYPE: PRT
<213> ORGANISM: Mus musculus

<400> SEQUENCE: 9

Arg Val Ile Pro Asn Asn Gly Gly Thr Ser Tyr Asn Gln Lys Phe Lys
 1               5                  10                  15

Gly

<210> SEQ ID NO 10
<211> LENGTH: 4
<212> TYPE: PRT
<213> ORGANISM: Mus musculus
```

```
<400> SEQUENCE: 10

Glu Gly Ile Tyr
  1

<210> SEQ ID NO 11
<211> LENGTH: 48
<212> TYPE: DNA
<213> ORGANISM: Mus musculus

<400> SEQUENCE: 11
agatctagtc agagccttgt acacagtaat ggaaacacct ttttacat              48

<210> SEQ ID NO 12
<211> LENGTH: 21
<212> TYPE: DNA
<213> ORGANISM: Mus musculus

<400> SEQUENCE: 12
acagtttcca accgattttc t                                           21

<210> SEQ ID NO 13
<211> LENGTH: 18
<212> TYPE: DNA
<213> ORGANISM: Mus musculus

<400> SEQUENCE: 13
actggctact acatacac                                               18

<210> SEQ ID NO 14
<211> LENGTH: 51
<212> TYPE: DNA
<213> ORGANISM: Mus musculus

<400> SEQUENCE: 14
cgtgttattc ctaacaatgg aggcactagt tacaaccaga agttcaaggg c           51

<210> SEQ ID NO 15
<211> LENGTH: 12
<212> TYPE: DNA
<213> ORGANISM: Mus musculus

<400> SEQUENCE: 15
gaagggatct ac                                                     12
```

METHODS FOR THE TREATMENT OF CANCER USING ANTI-CD40 ANTIBODIES

CROSS REFERENCE TO RELATED APPLICATIONS

This application is a division of U.S. patent application Ser. No. 10/846,981, filed May 14, 2004 (now U.S. Pat. No. 7,498, 032), which is a division of U.S. patent application Ser. No. 09/724,530, filed Nov. 28, 2000, now U.S. Pat. No. 6,843, 989, which is a division of U.S. patent application Ser. No. 09/328,296, filed Jun. 8, 1999, now U.S. Pat. No. 6,946,129, both of which are incorporated by reference herein in their entireties.

1. FIELD OF THE INVENTION

The present invention relates to methods and compositions for the treatment of diseases and disorders, including cancer, inflammatory diseases or disorders and diseases or disorders of the immune system, comprising administering a CD40 binding protein which enhances binding of CD40 ligand to CD40. CD40 binding proteins include recombinant/variant forms of monoclonal antibody S2C6 and derivatives thereof.

2. BACKGROUND OF THE INVENTION

CD40 is a cell surface phosphorylated glycoprotein that is expressed on a variety of cell types, including B cells, B cell malignancies, follicular dendritic cells, basal epithelial cells, and carcinomas. CD40 binds CD40 ligand ("CD40L"). CD40L is expressed on activated T cells during inflammation and cancer (Younes et al., 1998, Br. J. Haematol. 100:135-141; for a review see Grewal and Flavell, 1998, Annu. Rev. Immunol. 16:111-135). The interaction of CD40 with CD40L results in B cell activation and proliferation of normal B cells; however CD40-mediated signaling in B cell-derived tumor lines can result in activation-induced cell death. The strength of the activation signal is key to activation-induced tumor cell death (Grafton et al., 1997, Cell. Immunol. 182:45-56). Therefore, compositions and methods for increasing receptor-ligand interaction and strength of activation signal between CD40 and CD40L would be of great value in treating disease.

2.1 CD40 and CD40 Ligand

CD40 is a member of the TNF receptor superfamily. This family includes TNFrII, CD40, CD30, LMP-1, LTBr, ATAR, OX-40 and 4-1BB receptors. CD40 is constitutively expressed on B-lymphocytes, macrophages and dendritic cells and is induced by cytokine activation on fibroblasts, endothelial cells and epithelial cells (Van Kooten and Banchereau, 1997, Curr. Opin. Immunol., 9: 330-337). CD40 has also been shown to be highly expressed on many human carcinomas including lung, bladder, gastric, breast and ovarian cancers (Stamenkovic et al., 1989, EMBO J. 8:1403-1410).

The ligand for CD40 is a membrane protein that is expressed on activated T cells. Receptor binding of CD40L results in CD40 multimerization, the generation of activation signals (for antigen presenting cells such as dendritic cells, monocytes and B cells) and the generation of growth and differentiation signals (for cytokine-activated fibroblasts and epithelial cells). CD40 signals are transduced from the multimerized receptor via recruitment of a series of TNF receptor-associated factors ("TRAFs") (Kehry, 1996, J. Immunol. 156:2345-2348). Subsets of TRAFs interact differentially with TNF family members, including CD40, to provide stimuli to a wide variety of downstream pathways. TRAF1 and TRAF2 are implicated in the modulation of apoptosis (Speiser et al., 1997, J. Exp. Med. 185:1777-1783; Yeh et al., 1997, Immunity 7:715-725). TRAFs 2, 5, and 6 participate in proliferation and activation events, including NF-kB and c-Jun N-terminal kinase activation. In normal B cells, binding of CD40 recruits TRAF2 and TRAF3 to the receptor complex and induces down-regulation of other TRAFs (Kuhune et al., 1997, J. Exp. Med. 186: 337-342). The effects of CD40 binding are also dependent on membrane density (De Paoli et al., 1997, Cytometry 30:33-38). Importantly, unlike the proliferative response seen with normal primary B cells, CD40 binding on neoplastic B cells can result in growth inhibition and activation-induced cell death (Funakoshi et al., 1994, Blood 83:2787-2794). Thus, CD40 activation in the context of different cell types, transformation, resident TRAFs and co-stimuli can induce responses ranging from activation and proliferation to growth inhibition and apoptosis.

2.2 Anti-CD40 Antibodies

With at least one exception, the anti-CD40 monoclonal antibodies ("mAbs") described to date are of three general classes: (1) those that block CD40/CD40L interaction by at least 90% and have anti-neoplastic properties (Armitage et al., U.S. Pat. No. 5,674,492; Fanslow et al., 1995, Leukocyte Typing V, Schlossman et al., eds., 1:555-556); (2) those that antagonize signaling through CD40 (deBoer et al., U.S. Pat. No. 5,677,165); and (3) those that deliver a stimulatory signal through CD40 but do not increase the interaction between CD40 and CD40L, e.g., G28-5, (Ledbetter et al., U.S. Pat. No. 5,182,368; PCT Publication WO 96/18413).

One mAb, CD40.4 (5C3) (PharMingen, San Diego, Calif.), has been shown to increase the interaction between CD40 and CD40L by approximately 30-40% (Schlossman et al., eds., 1995, Leukocyte Typing V: White Cell Differentiation Antigens 1:547-556).

Armitage et al. (U.S. Pat. No. 5,674,492) describes methods using CD40 binding proteins, including mAb HuCD40-M2, that are capable of binding CD40 and inhibiting the binding of CD40 to CD40L, for preventing or treating disease characterized by neoplastic cells expressing CD40.

DeBoer et al. (U.S. Pat. No. 5,677,165) describes anti-CD40 mAbs that, being free of significant agonistic activity, bind to CD40 on the surface of B-cells, and block B-cell activation. An essential feature of U.S. Pat. No. 5,677,165 is that upon binding of the anti-CD40 mAb to human CD40 on the surface of normal human B cells, the growth or differentiation of normal human B cells is inhibited.

Ledbetter et al. (U.S. Pat. No. 5,182,368) describes a ligand, G28-5, that binds to the B cell surface antigen Bp50 (now designated CD40) and stimulates activated B cells to traverse the cell cycle such that B cell proliferation is augmented. However, G28-5 does not enhance activation of B cells in the presence of CD40L, and does not potentiate CD40/CD40L interaction.

S2C6 is an anti-CD40 mAb that was prepared against a human bladder carcinoma (Paulie et al., 1984, Cancer Immunol. Immunother. 17:165-179). S2C6 binds to the CD40 receptor expressed on a variety of cell types including B-lymphocytes, endothelial and epithelial cells. S2C6 has been shown to have specificity toward neoplastic urothelium and B cell-derived malignant lymphocytes. Reactivity with a prostatic carcinoma cell line, HS, and weak reactivity with a melanoma has also been shown (Paulie et al., 1984, Cancer Immunol. Immunother. 17:165-179). Studies have suggested the utility of S2C6 as a diagnostic marker for B cell malignancies (Paulie et al., 1984, Cancer Immunol. Immunother. 17:165-179; Paulie et al., 1985, Eur. J. Cancer. Clin. Oncol. 21:701-710). In addition to detecting B cell malignancies, S2C6 has been shown to deliver strong growth-promoting signals to B lymphocytes (Paulie et al., 1989, J. Immunol. 142:590-595).

S2C6 has agonistic activity on human peripheral B cells as demonstrated by its ability to stimulate primary B cell proliferation in a dose dependent manner (Paulie et al., 1989, J. Immunol. 142:590-595).

Although competition studies have shown that G28-5 and S2C6 bind the same or proximal epitopes, the antibodies have been determined to be functionally different based primarily on the stated magnitude of stimulation achieved by either mAb on previously stimulated tonsillar B cells (Clark and Ledbetter, 1986, Proc. Natl. Acad. Sci. USA 83:4494-4498; Ledbetter et al., U.S. Pat. No. 5,182,368). One hundred times more S2C6 compared to G28-5 was required to achieve tonsillar B cell activation under the specific conditions tested (Ledbetter et al., U.S. Pat. No. 5,182,368).

There is a need in the art for therapeutics with increased efficacy to treat or prevent cancer, activate or augment the immune system or treat or prevent an immune deficiency or disorder, a need provided by the present invention.

Citation or identification of any reference herein shall not be construed as an admission that such reference is available as prior art to the present invention.

3. SUMMARY OF THE INVENTION

Applicants have made the unexpected discovery of a new class of anti-CD40 antibodies that, in addition to delivering a stimulatory signal, enhances the interaction between CD40 and CD40L, enhances CD40L-mediated stimulation and has in vivo anti-neoplastic activity. Production and use of these antibodies and related molecules are facilitated by the inventors' cloning and sequencing of the variable region of mAb S2C6, and identification of the CDR and framework regions therein.

The present invention relates to molecules comprising the variable domain of mAb S2C6 or one or more of the complementarity-determining regions (CDRs) thereof having novel sequences (SEQ ID NO: 3, 4, 8, 9 or 10), which molecules (a) immunospecifically bind CD40 and (b) comprise one or more substitutions or insertions in primary amino acid sequence relative to native monoclonal antibody S2C6 as secreted by the hybridoma deposited with the ATCC and assigned accession number PTA-110. In a specific embodiment, the molecules are not native monoclonal antibody S2C6 and do not comprise the native heavy or light chain of said monoclonal antibody S2C6. In a specific embodiment, the molecule is an antibody. In another embodiment, the antibody is not isotype IgG1. In another specific embodiment, the molecule comprises a light chain variable domain, the amino acid sequence of SEQ ID NO:2, or a heavy chain variable domain, the amino acid sequence of SEQ ID NO:7.

The invention further relates to chimeric/fusion proteins comprising a fragment of mAb S2C6 fused to an amino acid sequence of a second protein, as well as to molecules wherein a fragment of mAb S2C6 is covalently bound (e.g., by use of a crosslinking agent) to another chemical structure. In a specific embodiment, a molecule is provided that immunospecifically binds CD40, which molecule comprises the heavy and/or light chain variable domain of mAb S2C6 fused to a second protein comprising the amino acid sequence of bryodin 1 (BD1).

The invention further relates to proteins comprising an amino acid sequence that has at least 95% identity to SEQ ID NO:2, SEQ ID NO:3, SEQ ID NO:4, SEQ ID NO:7, SEQ ID NO:8, SEQ ID NO:9, or SEQ ID NO:10, which proteins (a) immunospecifically bind CD40 and (b) comprise one or more substitutions or insertions in primary amino acid sequence relative to native monoclonal antibody S2C6 as secreted by the hybridoma deposited with the ATCC and assigned accession number PTA-110. In a specific embodiment, the proteins are not native monoclonal antibody S2C6 and do not comprise the native heavy or light chain of said monoclonal antibody S2C6.

The invention further relates to purified proteins, which proteins (a) compete for binding to CD40 with monoclonal antibody S2C6 as secreted by the hybridoma deposited with the ATCC and assigned accession number PTA-110, (b) increase the binding of CD40 ligand to CD40 by at least 45%, and (c) comprise one or more substitutions or insertions in primary amino acid sequence relative to native monoclonal antibody S2C6 as secreted by the hybridoma deposited with the ATCC and assigned accession number PTA-110. In a specific embodiment, the proteins are not native monoclonal antibody S2C6 and do not comprise the native heavy or light chain of said monoclonal antibody S2C6.

The invention further relates to nucleic acids encoding such molecules and proteins or which hybridize to a DNA consisting of the nucleotide sequence encoding such proteins; recombinant cells comprising such molecules and proteins; and methods of producing such proteins.

In an embodiment, the isolated nucleic acid comprises a nucleotide sequence encoding a protein comprising (a) a heavy chain variable domain of monoclonal antibody S2C6 as secreted by the hybridoma deposited with the ATCC and assigned accession number PTA-110, and (b) a human constant region.

In an embodiment, the isolated nucleic acid comprises a nucleotide sequence encoding a protein comprising (a) a light chain variable domain of monoclonal antibody S2C6 as secreted by the hybridoma deposited with the ATCC and assigned accession number PTA-110, and (b) a human constant region.

The invention further relates to recombinant cells containing a recombinant nucleic acid vector comprising a nucleotide sequence encoding a protein, which protein competes for binding to CD40 with monoclonal antibody S2C6 as secreted by the hybridoma deposited with the ATCC and assigned accession number PTA-110, and which protein increases the binding of CD40 ligand to CD40 by at least 45%. The invention also provides methods of producing such proteins comprising growing such cells such that the protein is expressed by the cell, and recovering the expressed protein.

The invention further relates to recombinant cells containing a recombinant nucleic acid vector comprising SEQ ID NO:1, SEQ ID NO:6, SEQ ID NO:11, SEQ ID NO:12, SEQ ID NO:13, SEQ ID NO:14, or SEQ ID NO:15 and methods of producing proteins comprising growing such cells, such that a protein encoded by the nucleotide sequence is expressed by the cell, and recovering the expressed protein.

Pharmaceutical compositions containing the molecules and antibodies of the invention, preferably in purified form, are also provided. In particular embodiments, the invention relates to pharmaceutical compositions comprising a molecule comprising SEQ ID NO:2, SEQ ID NO:3, SEQ ID NO:4, SEQ ID NO:7, SEQ ID NO:8, SEQ ID NO:9, or SEQ ID No:10, which molecule (i) immunospecifically binds CD40, (ii) increases the binding of CD40 ligand to CD40, and (iii) comprises one or more substitutions or insertions in primary amino acid sequence relative to native monoclonal antibody S2C6 as secreted by the hybridoma deposited with the ATCC and assigned accession number PTA-110; and a pharmaceutically acceptable carrier. In a specific embodiment, the molecule is not native monoclonal antibody S2C6 and does not comprise the native heavy or light chain of said monoclonal antibody S2C6.

The invention further relates to pharmaceutical compositions comprising a purified protein, which protein (i) competes for binding to CD40 with mAb S2C6 as secreted by the hybridoma deposited with the ATCC and assigned accession number PTA-110, (ii) increases the binding of CD40 ligand to CD40 by at least 45%, and (iii) comprises one or more substitutions or insertions in primary amino acid sequence to relative to native monoclonal antibody S2C6 as deposited with the ATCC and assigned accession number PTA-110; and a pharmaceutically acceptable carrier. In a specific embodiment, the protein is not native monoclonal antibody S2C6 and does not comprise the native heavy or light chain of said monoclonal antibody S2C6.

In specific embodiments, the pharmaceutical compositions of the invention contain the molecules or antibodies of the invention in an amount effective for the treatment or prevention of cancer, or an amount effective for activating or augmenting an immune response, or an amount such that the immune response of the subject is activated or augmented.

In specific embodiments, the pharmaceutical compositions of the invention further comprise CD40 ligand. In a specific embodiment, the pharmaceutical composition comprises in an amount effective for the treatment or prevention of cancer or an immune disorder, or for activating or augmenting an immune response: (a) a molecule that immunospecifically binds CD40, which molecule increases the binding of CD40 ligand to CD40; (b) CD40 ligand; and (c) a pharmaceutically acceptable carrier. In this embodiment, for example, the molecule can be native mAb S2C6 or native mAb 5C3 or an S2C6 derivative as described herein.

The invention further relates to methods for the treatment or prevention of cancer in a subject, for activating or augmenting an immune response in a subject, or for the treatment or prevention of an immune deficiency or disorder in a subject comprising administering to the subject a therapeutically effective amount of the molecules or antibodies of the invention, e.g., an amount of a molecule comprising SEQ ID NO:2, SEQ ID NO:3, SEQ ID NO:4, SEQ ID NO:7, SEQ ID NO:8, SEQ ID NO:9, or SEQ ID NO:10, which molecule (i) immunospecifically binds CD40, (ii) increases the binding of CD40 ligand to CD40 by at least 45%, and comprises one or more substitutions or insertions in primary amino acid sequence relative to native monoclonal antibody S2C6 as secreted by the hybridoma deposited with the ATCC and assigned accession number PTA-110. In a specific embodiment, the molecule is not native monoclonal antibody S2C6 and does not comprise the native heavy or light chain of said monoclonal antibody S2C6.

The invention further relates to methods for the treatment or prevention of cancer in a subject, for activating or augmenting an immune response in a subject, or for the treatment or prevention of an immune deficiency or disorder in a subject comprising administering to the subject a purified protein, which protein (i) competes for binding to CD40 with monoclonal antibody S2C6 as secreted by the hybridoma deposited with the ATCC and assigned accession number PTA-110, (ii) increases the binding of CD40 ligand to CD40 by at least 45%, and (iii) comprises one or more substitutions or insertions in the primary amino acid sequence relative to native monoclonal antibody S2C6 as deposited with the ATCC and assigned accession number PTA-10. In a specific embodiment, the protein is not native monoclonal antibody S2C6 and does not comprise the native heavy or light chain of said monoclonal antibody S2C6.

In specific embodiments, the methods of the invention further comprise administering CD40 ligand to the subject.

The invention further relates to a method for the treatment or prevention of cancer or an immune disorder in a subject comprising administering to the subject, in an amount effective for said treatment or prevention: (a) a molecule that immunospecifically binds CD40, which molecule increases the binding of CD40 ligand to CD40; and (b) CD40 ligand, in which the molecule can be native mAb S2C6 or native mAb 5C3 or any of the S2C6 derivatives described herein.

In a preferred embodiment, the subject is a human.

The invention further relates to a transgenic non-human animal, plant, or an isolated cell containing one or more transgenes encoding a protein, which protein competes for binding to CD40 with monoclonal antibody S2C6 as secreted by the hybridoma deposited with the ATCC and assigned accession number PTA-110, and which protein increases the binding of CD40 ligand to CD40 by at least 45%.

4. BRIEF DESCRIPTION OF THE FIGURES

FIG. 1. Structure of the light chain variable region of S2C6. The nucleotide (SEQ ID NO:1) and amino acid (SEQ ID NO:2) sequences of the light chain variable region ("$V_L$") are shown.

FIG. 2. Structure of the heavy chain variable region of S2C6. The nucleotide (SEQ ID NO:6) and amino acid (SEQ ID NO:7) sequences of the heavy chain variable region ("$V_H$") of S2C6 are shown.

FIGS. 3A-3B. Structure of variable regions of S2C6. (A) The amino acid sequence (SEQ ID NO:2) of S2C6 $V_L$ is shown. (B) The amino acid sequence (SEQ ID NO:7) of S2C6 $V_H$ is shown. Complementarity-determining regions ("CDR") are underlined. The sequences of the four framework regions, adjacent to the CDRs, are shown. The amino acid sequences of $V_L$ CDRs 1-3 correspond to SEQ ID NOS: 3-5, respectively. The amino acid sequences of $V_H$ CDRs 1-3 correspond to SEQ ID NOS:8-10, respectively.

FIG. 4. S2C6 mAb augments CD40-Ig binding to CD40L-expressing Jurkat T cells. CD40-Ig (a soluble fusion protein of CD40 and human immunoglobulin) binding to surface CD40L was done in the presence of increasing concentrations of anti-CD40 monoclonal antibody ("mAb"). mAbs were pre-incubated for 1 hour with CD40-Ig followed by incubation for 1 hour with CD40L-expressing target cells. CD40-Ig binding to target cells was detected by flow cytometry using a fluorescein isothiocyanate ("FITC")-labeled anti-human Ig. The extent of CD40/CD40L binding was then determined from log mean fluorescent intensity ("MFI"). MFI minus background of each population is shown.

Figure 5:
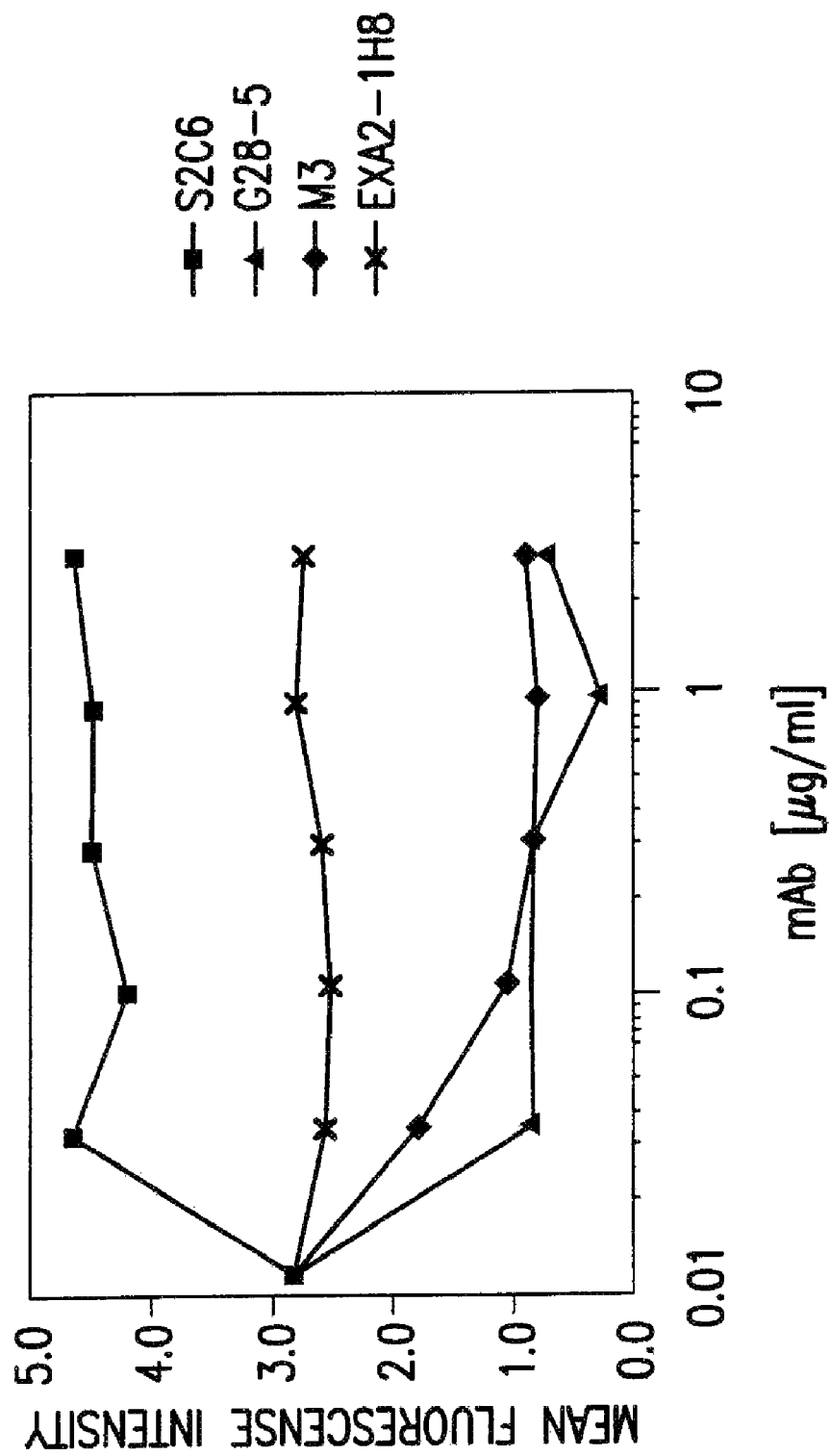

FIG. 5. S2C6 mAb augments binding of soluble CD40L to B cell surface CD40. Ramos B cells, a human B cell lymphoma, were incubated in the presence of increasing concentrations of an anti-CD40 mAb: S2C6, G28-5, or M3 or an irrelevant control mAb, EXA2-1H8. The mAbs were pre-incubated for 1 hour with CD40-expressing target cells. Binding of the FITC-labeled CD40L to B cells was then detected directly by flow cytometry. The extent of CD40/CD40L binding was then determined from log mean fluorescent intensity. MFI minus background of each population is shown.

Figure 6:
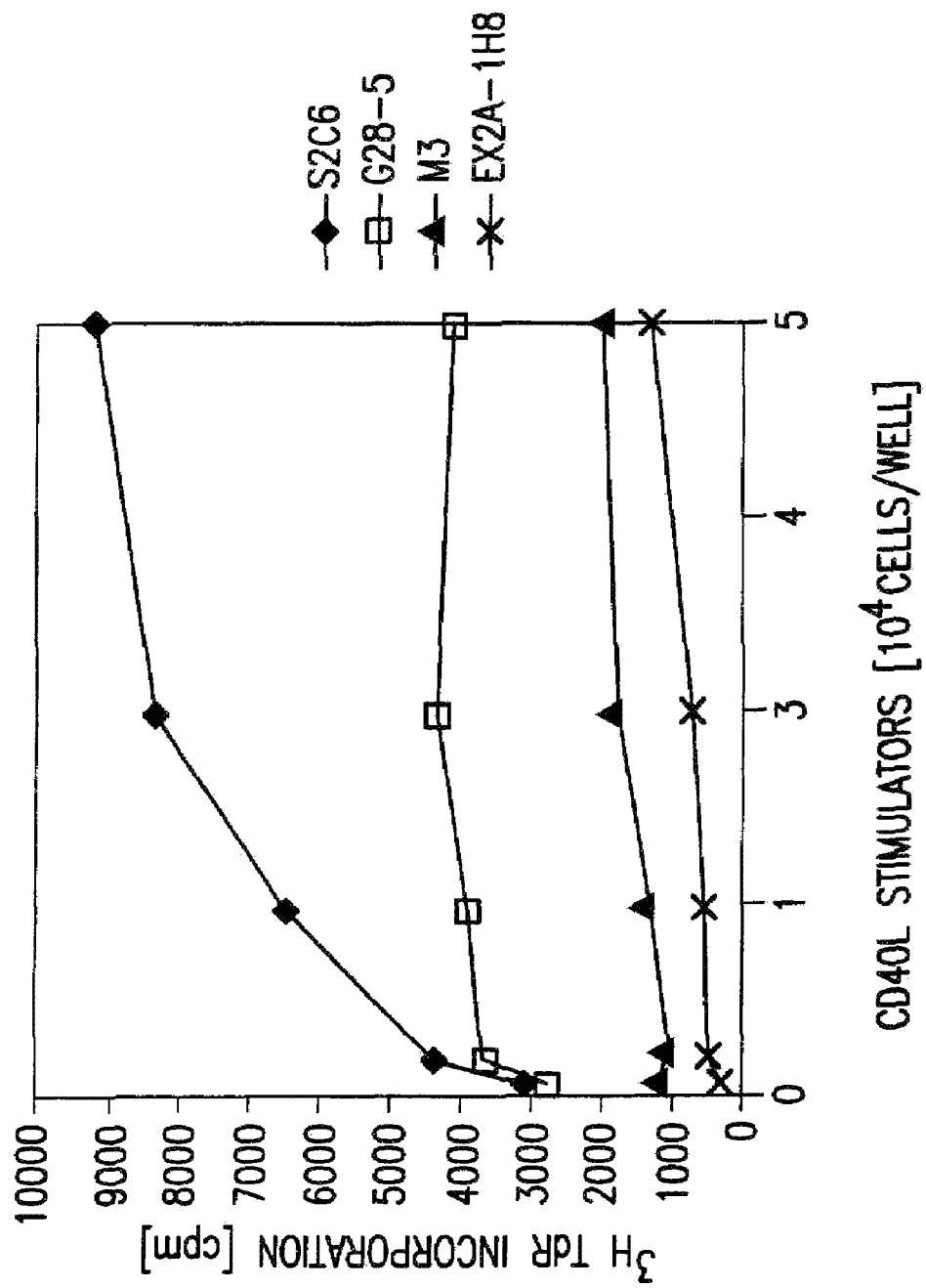

FIG. 6. S2C6 enhances proliferative response of primary human peripheral B cells in the presence of CD40L$^+$ stimulator cells and an anti-CD40 mAb. Peripheral B cells ($1 \times 10^5$/ well) were combined with increasing numbers of non-proliferative CD40L+ Jurkat T stimulator cells and 30 ng/ml of an anti-CD40 mAb. S2C6, G28-5, or M3 or the control mAb, EXA2-1H8. B cell proliferation was measured by .sup.3H-TdR incorporation at 72 h following addition of stimulus.

Figure 7:
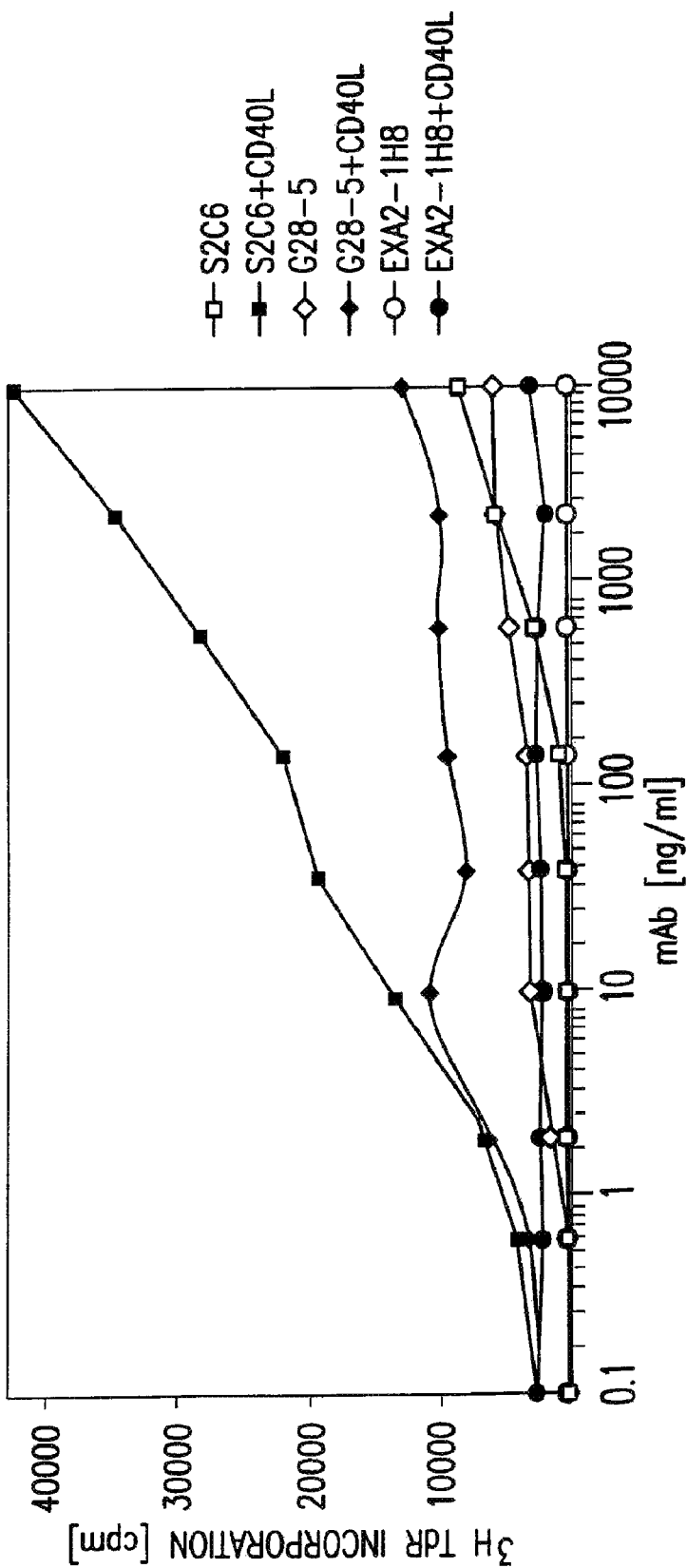

FIG. 7. Comparative proliferative response of primary human peripheral B cells to an anti-CD40 mAb in the presence or absence of CD40L. Peripheral B cells were combined with non-proliferative CD40L+ stimulator cells at a fixed ratio of 4:1 and increasing concentrations of an anti-CD40 mAb: S2C6 G28-5 or the control antibody, EXA2-1HB. B cell proliferation was measured by $^3$H-TdR incorporation at 72 h following addition of stimulus.

Figure 8A:
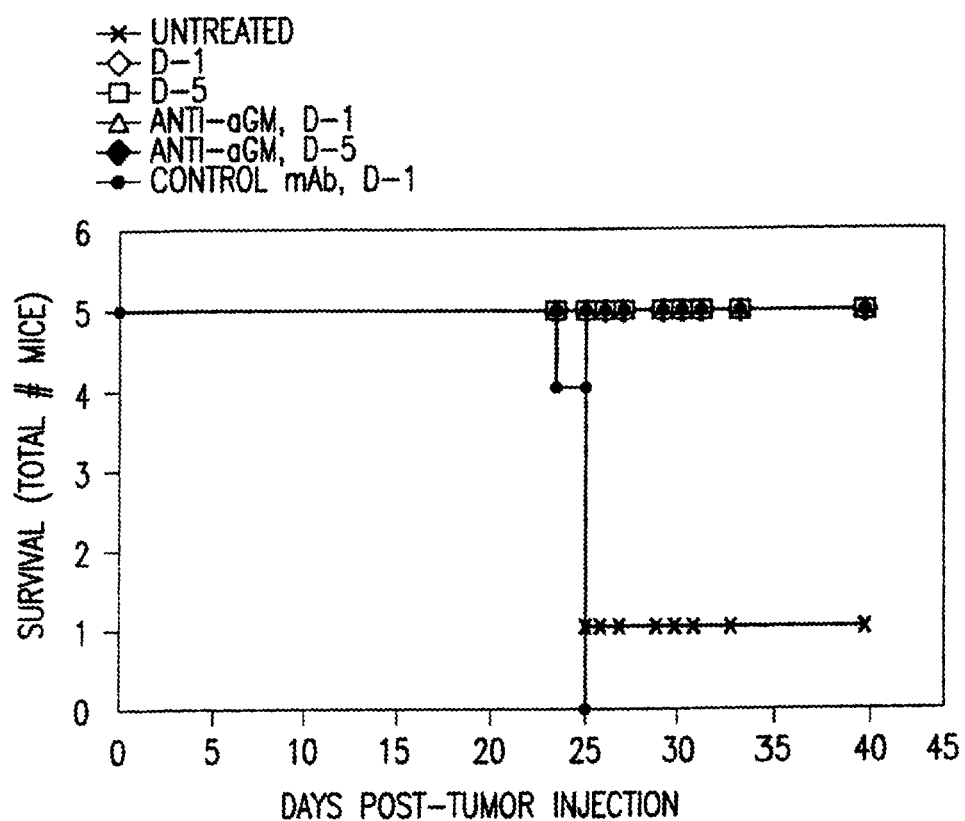
Figure 8B:
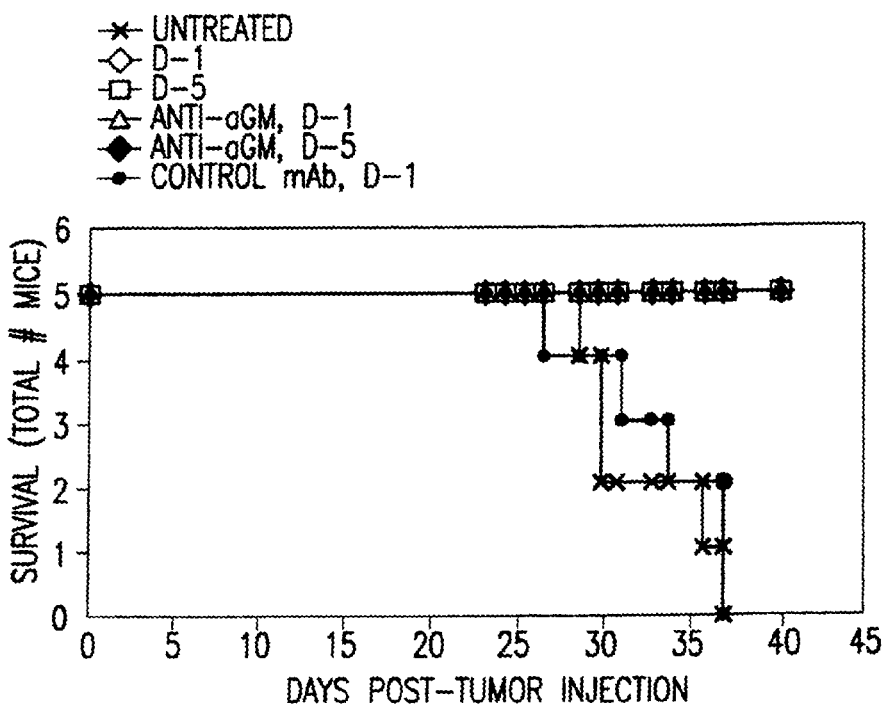
Figure 8C:
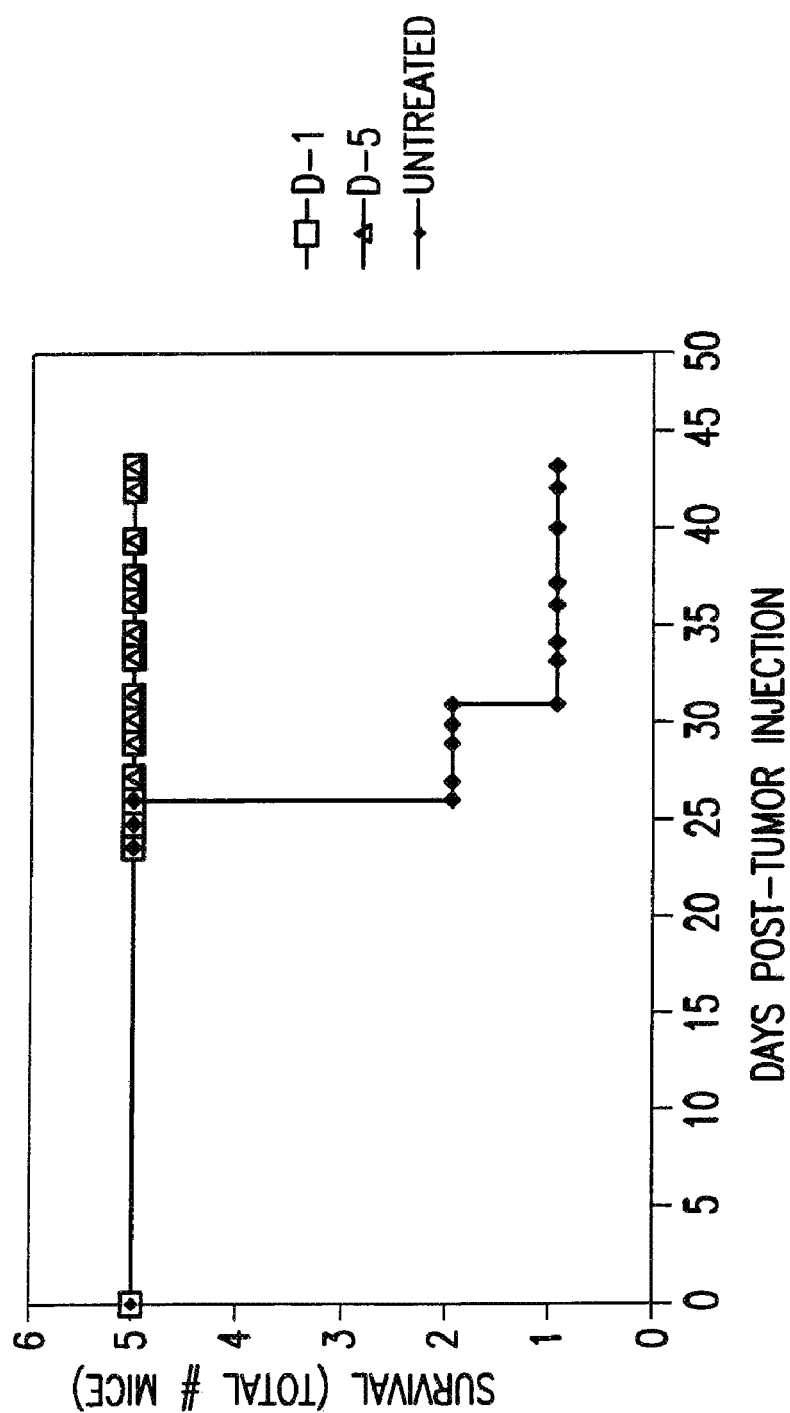

FIG. 8. Anti-tumor activity of mAb S2C6 in vivo. (A) Anti-tumor activity of S2C6 against Ramos human B cell non-Hodgkin's lymphoma, (B) Anti-tumor activity of S2C6 against HS Sultan multiple myeloma, or (C) Anti-tumor activity of S2C6 against IM-9 multiple myeloma was assessed. SCID mice (5/group) were pretreated or not with anti-asialo-GM1 to inhibit natural killer ("NK") activity and treated with mAb on day 1 or day 5 following injection of $1 \times 10^6 - 2 \times 10^6$ tumor cells. Solid lines indicate the number of surviving mice over time.

FIG. 9. BD1-S2C6 sFv specifically binds to immobilized CD40-Ig in ELISA. BD1-S2C6 sFv (single-chain anti-CD40 immunotoxin consisting of bryodin 1 (BD1) fused to the variable region of monoclonal antibody S2C6) was expressed in *E. coli* as inclusion bodies, denatured and refolded. The refolded protein was then isolated using Blue Sepharoe followed by affinity chromatography over immobilized CD40-Ig. The purified protein was then tested for binding to immobilized CD40-Ig in ELISA. Microtiter plates were coated with CD40-Ig at 0.5 μg/ml followed by the addition of dilutions of purified BD1-S2C6 sFv in the presence of 25 μg/ml S2C6 mAb (▲), 25 μg/ml control antibody BR96 (●), or no excess antibody (■). Binding of BD1-S2C6 sFv to the immobilized receptor was detected by the addition of BD1-specific rabbit antiserum followed by the addition of horseradish peroxidase conjugated goat anti-rabbit Ig. The binding of BD1-S2C6 sFv to CD40-Ig was completely inhibited by the addition of excess S2C6 mAb but not by the addition of the control mAb.

5. DETAILED DESCRIPTION OF THE INVENTION

The present invention relates to proteins encoded by and nucleotide sequences of S2C6 genes. The invention further relates to fragments and other derivatives and analogs of such S2C6 proteins and nucleic acids. In various specific embodiments, the molecules (e.g., antibodies) of the invention comprise all or a portion of mAb S2C6 (the light chain and/or heavy chain, or light chain CDR 1 (SEQ ID NO:3) and/or 2 (SEQ ID NO:4), and/or heavy chain CDR 1 (SEQ ID NO:8), 2 (SEQ ID NO:9), and/or 3 (SEQ ID NO:10), or light chain CDR3 (SEQ ID NO:5) in combination with any of the other CDRs and/or one or more of the four heavy chain and four light chain framework regions, provided that such molecules are not native mAB S2C6 as deposited with the ATCC and assigned accession number PTA-110 or the heavy or light chain thereof. Such molecules may differ from S2C6 in sequence and/or in post-translational modification (glycosylation, amidation, peptide bonding or cross-linking to a non-S2C6 sequence, etc.). In various specific embodiments, a molecule of the invention immunospecifically binds CD40 (or when multimerized immunospecifically binds CD40), competes with native S2C6 for binding to CD40, and/or increases the binding of CD40 ligand to CD40 by at least 45%, 50%, 60% or 65%. Nucleic acids encoding such molecules, e.g., S2C6 fragments or derivatives, are also within the scope of the invention, as well as nucleic acids encoding native mAb S2C6. Production of the foregoing proteins, e.g., by recombinant methods, is provided.

The invention also relates to S2C6 proteins and derivatives including but not limited to fusion/chimeric proteins which are functionally active, i.e., which are capable of displaying one or more known functional activities associated with a full-length S2C6 mAb. Such functional activities include but are not limited to ability to bind CD40, delivery of a stimulatory signal to the CD40 signaling pathway (e.g., so as to cause B cell proliferation), potentiation of the interaction of CD40L with CD40; ability to inhibit tumor growth; and ability to induce an immune response.

Antibodies to CD40 comprising S2C6, its derivatives and analogs including but not limited to humanized antibodies; single chain antibodies; bispecific antibodies; and antibodies conjugated to chemotherapeutic agents or biological response modifiers, are additionally provided.

The invention further relates to methods of treating or preventing cancer, inflammatory diseases and disorders of the immune system comprising administering a composition of the invention alone or in combination with CD40L.

The invention is illustrated by way of examples set forth in sections 6-9 below which disclose, inter alia, the cloning and characterization of S2C6 genes; the potentiation of the CD40/CD40L interaction; inhibition of tumor growth; and binding of a single-chain anti-CD40 immunotoxin to CD40-Ig.

For clarity of disclosure, and not by way of limitation, the detailed description of the invention is divided into the subsections which follow.

5.1 Isolation of S2C6 Genes

The invention relates to the nucleotide sequences of S2C6 nucleic acids. In specific embodiments, S2C6 nucleic acids comprise the cDNA sequences of SEQ ID NOS:1 and 6, or nucleic acids encoding an S2C6 protein (e.g., a protein having the sequence of SEQ ID NOS:2 and 7). The invention provides purified nucleic acids consisting of at least 8 nucleotides (i.e., a hybridizable portion) of an S2C6 gene sequence; in other embodiments, the nucleic acids consist of at least 25 (contiguous) nucleotides, 50 nucleotides, 100, or 200 nucleotides of an S2C6 sequence, or a full-length S2C6 variable region coding sequence. In the same or other embodiments, the nucleic acids are smaller than 50, 75, 100, or 200 or 5000 nucleotides in length. Nucleic acids can be single or double stranded. The invention also relates to nucleic acids hybridizable to or complementary to the foregoing sequences or their reverse complements, and in particular, such nucleic acids that encode proteins that bind to CD40, compete with S2C6 for binding to CD40, and/or increase the binding of CD40 ligand to CD40 by at least 45%, 50%, 60%, or 65%. In specific aspects, nucleic acids are provided which comprise a sequence complementary to at least 10, 25, 50, 100, or 200 nucleotides or the entire coding region of an S2C6 variable region gene.

Nucleic acids encoding derivatives and analogs of S2C6 proteins are additionally provided. As is readily apparent, as used herein, a "nucleic acid encoding a fragment or portion of an S2C6 protein" shall be construed as referring to a nucleic acid encoding only the recited fragment or portion of the S2C6 protein and not the other contiguous portions of the S2C6 protein as a continuous sequence.

5.2 Cloning Procedures

Specific embodiments for the cloning of an S2C6 gene follow. In a specific embodiment, total RNA is isolated from a mAb S2C6-producing hybridoma and polymerase chain reaction is used to amplify desired variable region sequences, using primers based on the sequences disclosed herein. For an illustrative example, see Section 6, infra. By way of another example, mRNA is isolated from a mAb S2C6-producing hybridoma, cDNA is made and ligated into an expression vector (e.g., a bacteriophage derivative) such that it is capable of being expressed by the host cell into which it is then introduced. Various screening assays can then be used to select for the expressed product. In one embodiment, selection is on the basis of hybridization to a labeled probe representing a portion of an S2C6 gene or its RNA or a fragment thereof (Benton and Davis, 1977, Science 196:180; Grunstein and Hogness, 1975, Proc. Natl. Acad. Sci. U.S.A. 72:3961). Those DNA fragments with substantial homology to the probe will hybridize. It is also possible to identify the appropriate fragment by restriction enzyme digestion(s) and comparison of fragment sizes with those expected according to a known restriction map if such is available. Further selection can be carried out on the basis of the properties of the gene.

Alternatively, the presence of the desired gene may be detected by assays based on the physical, chemical, or immunological properties of its expressed product. For example, cDNA clones, or DNA clones which hybrid-select the proper mRNAs, can be selected and expressed to produce a protein that has, e.g., similar or identical electrophoretic migration, isoelectric focusing behavior, proteolytic digestion maps, or functional activity, as known for an S2C6 protein. For example, ability to bind CD40 can be detected in an ELISA (enzyme-linked immunosorbent assay)-type procedure.

An S2C6 gene can also be identified by mRNA selection using nucleic acid hybridization followed by in vitro translation. In this procedure, fragments are used to isolate complementary mRNAs by hybridization. Functional assays (e.g., binding to CD40, etc.) of the in vitro translation products of the isolated products of the isolated mRNAs identifies the mRNA and, therefore, the complementary DNA fragments that contain the desired sequences.

In another embodiment, the S2C6 cDNA can be chemically synthesized from the sequence disclosed herein. Other methods of isolating S2C6 genes known to the skilled artisan can be employed.

The identified and isolated S2C6 gene/cDNA can then be inserted into an appropriate cloning vector. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as PBR322 or pUC plasmid derivatives or the Bluescript vector (Stratagene). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and an S2C6 gene may be modified by homopolymeric tailing, or by PCR with primers containing the appropriate sequences. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionization, can be done before insertion into the cloning vector.

In specific embodiments, transformation of host cells with recombinant DNA molecules that incorporate an isolated S2C6 gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The S2C6 sequences provided by the instant invention include those nucleotide sequences encoding substantially the same amino acid sequences as found in native S2C6 variable regions, and those encoded amino acid sequences with functionally equivalent amino acids, as well as those encoding other S2C6 derivatives or analogs, as described below for S2C6 derivatives and analogs.

5.3 Expression of S2C6 Genes

The nucleotide sequence coding for an S2C6 protein or a functionally active analog or fragment or other derivative thereof (see Section 5.6), can be inserted into an appropriate expression vector, i.e., a vector which contains the necessary elements for the transcription and translation of the inserted protein-coding sequence. The necessary transcriptional and translational signals can also be supplied by the native S2C6 gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA; transgenic plants or transgenic non-human animals. The expression elements of vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of a nucleic acid sequence encoding an S2C6 protein or peptide fragment may be regulated by a second nucleic acid sequence so that the S2C6 protein or peptide is expressed in a host transformed with the recombinant DNA molecule. For example, expression of an S2C6 protein may be controlled by any promoter/enhancer element known in the art. Promoters that are not native S2C6 gene promoters which may be used to control S2C6 gene expression include, but are not limited to, the SV40 early promoter region (Benoist and Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); prokaryotic expression vectors such as the β-lactamase promoter (Villa-Kamaroff et al., 1978, Proc. Natl. Acad. Sci. U.S.A. 75:3727-3731), or the lac promoter (DeBoer et al., 1983, Proc. Natl. Acad. Sci. U.S.A. 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus $^{35}$S RNA promoter (Gardner et al., 1981, Nucl. Acids Res. 9; 2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); a gene control region which is active in pancreatic beta cells (Hanahan, 1985, Nature 315: 115-122), an immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

In a specific embodiment, a vector is used that comprises a promoter operably linked to an S2C6 gene nucleic acid, one or more origins of replication, and, optionally, one or more selectable markers (e.g., an antibiotic resistance gene).

Expression vectors containing S2C6 gene inserts can be identified by three general approaches: (a) nucleic acid hybridization; (b) presence or absence of "marker" gene functions; and (c) expression of inserted sequences. In the first approach, the presence of an S2C6 gene inserted in an expression vector can be detected by nucleic acid hybridization using probes comprising sequences that are homologous to an inserted S2C6 gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of an S2C6 gene in the vector. For example, if the S2C6 gene is inserted within the marker gene sequence of the vector, recombinants containing the S2C6 insert can be identified by the absence of the marker gene function. In the third approach, recombinant expression vectors can be identified by assaying the S2C6 product expressed by the recombinant. Such assays can be based, for example, on the physical or functional properties of the S2C6 protein in in vitro assay systems, e.g., potentiation of CD40L binding with CD40; stimulation of proliferation of normal B cells; inhibition of tumor growth.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda phage), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered S2C6 protein may be controlled. Furthermore, different host cells have characteristic and specific mechanisms for the translational and post-translational processing and modification (e.g., glycosylation, phosphorylation of proteins. Appropriate cell lines or host systems can be chosen to ensure the desired modification and processing of the foreign protein expressed. For example, expression in a bacterial system can be used to produce a non-glycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

In specific embodiments, the S2C6-related protein that is expressed is an antibody or fragment or derivative thereof. The recombinant antibody may contain a recombinant light chain variable domain, a recombinant heavy chain variable domain, or both. In a specific embodiment, both light and heavy chains or derivatives thereof are recombinantly expressed by a cell (see e.g., U.S. Pat. No. 4,816,397 dated Mar. 28, 1989 by Boss et al.) A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA; transgenic plants or transgenic non-human animals.

5.4 Identification and Purification of Gene Products

In particular aspects, the invention provides amino acid sequences of S2C6 proteins and fragments and derivatives thereof which comprise a complementarity-determining region (CDR) or which are otherwise functionally active, as well as nucleic acid sequences encoding the foregoing. "Functionally active" S2C6 material as used herein refers to that material displaying one or more functional activities associated with a full-length (native) S2C6 protein, e.g., binding to CD40; stimulation of proliferation of normal B cells; inhibition of tumor growth; increase the binding of CD40 ligand to CD40 by at least 45%.

In specific embodiments, the invention provides fragments of an S2C6 protein consisting of at least 6 amino acids, 10 amino acids, 20 amino acids, 50 amino acids, 75 amino acids or of at least 100 amino acids and nucleic acids encoding the foregoing.

Once a recombinant which expresses the S2C6 gene sequence is identified, the gene product can be analyzed. This is achieved by assays based on the physical or functional properties of the product, including radioactive labeling of the product followed by analysis by gel electrophoresis, immunoassay; stimulation of proliferation of normal B cells; CD40 binding assays, promotion of the binding of CD40 ligand to CD40, inhibition of tumor growth, etc.

Once the S2C6 protein is identified, it may be isolated and purified by standard methods including chromatography (e.g., ion exchange, affinity, and sizing column chromatography), centrifugation, differential solubility, or by any other standard technique for the purification of proteins. The functional properties may be evaluated using any suitable assay (see Section 5.7).

Alternatively, the S2C6 protein or derivative thereof can be synthesized by standard chemical methods known in the art based on the sequence disclosed herein (e.g., see Hunkapiller et al., 1984, Nature 310:105-111).

In a specific embodiment of the present invention, such S2C6 proteins, whether produced by recombinant DNA techniques or by chemical synthetic methods or by purification of native proteins, include but are not limited to those containing, as a primary amino acid sequence, all or part of the amino acid sequence substantially as depicted in FIGS. 3A-3B (SEQ ID NOS:2 and 7), as well as fragments and other derivatives, and analogs thereof, including proteins homologous thereto.

5.5 Structure of S2C6 Genes and Proteins

The structure of S2C6 genes and proteins of the invention can be analyzed by various methods known in the art. Some examples of such methods are described below.

5.5.1 Genetic Analysis

The cloned DNA or cDNA corresponding to an S2C6 gene can be analyzed by methods including but not limited to Southern hybridization (Southern, 1975, J. Mol. Biol. 98:503-517), Northern hybridization (see e.g., Freeman et al., 1983, Proc. Natl. Acad. Sci. U.S.A. 80:4094-4098), restriction endonuclease mapping (Maniatis, 1982, Molecular Cloning, A Laboratory Manual, Cold Spring Harbor Laboratory Press, Cold Spring Harbor, N.Y.), and DNA sequence analysis. Accordingly, this invention provides nucleic acid probes recognizing an S2C6 gene. For example, polymerase chain reaction (PCR; U.S. Pat. Nos. 4,683,202, 4,683,195 and 4,889,818; Gyllenstein et al., 1988, Proc. Natl. Acad. Sci. U.S.A. 85:7652-7656; Ochman et al., 1988, Genetics 120: 621-623; Loh et al., 1989, Science 243:217-220) followed by Southern hybridization with an S2C6 gene-specific probe can allow the detection of an S2C6 gene in DNA or cDNA from a cell (e.g., hybridoma). Methods of amplification other than PCR are commonly known and can also be employed. The stringency of the hybridization conditions for both Southern and Northern hybridization can be manipulated to ensure detection of nucleic acids with the desired degree of relatedness to the specific S2C6 gene probe used. Modifications of these methods and other methods commonly known in the art can be used.

Restriction endonuclease mapping can be used to roughly determine the genetic structure of an S2C6 gene. Restriction maps derived by restriction endonuclease cleavage can be confirmed by DNA sequence analysis.

DNA sequence analysis can be performed by any techniques known in the art, including but not limited to the method of Maxam and Gilbert (1980, Meth. Enzymol. 65:499-560), the Sanger dideoxy method (Sanger et al., 1977, Proc. Natl. Acad. Sci. U.S.A. 74:5463), the use of T7 DNA polymerase (Tabor and Richardson, U.S. Pat. No. 4,795,699), or use of an automated DNA sequenator (e.g., Applied Biosystems, Foster City, Calif.).

5.5.2 Protein Analysis

The amino acid sequence of an S2C6 protein can be derived by deduction from the DNA sequence, or alternatively, by direct sequencing of the protein, e.g., with an automated amino acid sequencer.

An S2C6 protein sequence can be further characterized by a hydrophilicity analysis (Hopp and Woods, 1981, Proc. Natl. Acad. Sci. U.S.A. 78:3824). A hydrophilicity profile can be used to identify the hydrophobic and hydrophilic (potentially immunogenic) regions of the S2C6 protein and the corresponding regions of the gene sequence which encode such regions.

Secondary, structural analysis (Chou and Fasman, 1974, Biochemistry 13:222) can also be done, to identify regions of an S2C6 protein that assume specific secondary structures.

Manipulation, translation, and secondary structure prediction, open reading frame prediction and plotting, as well as determination of sequence homologies, can also be accomplished using computer software programs available in the art.

5.6 mAb S2C6 Antibody Derivatives

Described herein are methods for the production of S2C6 antibody derivatives capable of immunospecifically binding CD40.

Such antibodies include but are not limited to monoclonal, humanized, chimeric, single chain, bispecific, Fab fragments, $F(ab')_2$ fragments, fragments produced by a Fab expression library, anti-idiotypic (anti-Id) antibodies, and epitope-binding fragments of any of the above.

For preparation of additional monoclonal antibodies to CD40, any technique that provides for the production of antibody molecules by continuous cell lines in culture may be used. These include but are not limited to the hybridoma technique of Kohler and Milstein, (1975, Nature 256, 495-497; and U.S. Pat. No. 4,376,110), the human B-cell hybridoma technique (Kozbor et al., 1983, Immunology Today 4, 72; Cole et al., 1983, Proc. Natl. Acad. Sci. USA 80, 2026-2030), and the EBV-hybridoma technique to produce human monoclonal antibodies (Cole et al., 1985, Monoclonal Antibodies And Cancer Therapy, Alan R. Liss, Inc., pp. 77-96). Such antibodies or other anti-CD40 antibodies available in the art may, e.g., be used as the basis from which to clone and thus supply complementary light chain if a S2C6 heavy chain is to be recombinantly expressed (the two chains may be recombinantly expressed in the same cell or combined in vitro after separate expression and purification); alternatively, a light chain from an antibody of any specificity may be used. Nucleic acids (e.g., a plasmid) encoding a S2C6 heavy chain or encoding a molecule comprising a S2C6 heavy chain variable domain can be transferred into a cell expressing an antibody light chain or molecule comprising an antibody light chain, for expression of a multimeric protein; the antibody light chain can be recombinant or non-recombinant, and may or may not have anti-CD40 specificity. Alternatively, S2C6 heavy chains or molecules comprising the variable region thereof or a CDR thereof can optionally be expressed and used without the presence of a complementary light chain or light chain variable region. In various embodiments, the invention provides a S2C6 heavy chain with CD40 binding affinity, or a molecule consisting of or (alternatively) comprising one or more copies of heavy chain CDR 1, 2, and/or 3 (corresponding to SEQ ID NO:8, 9, and/or 10, respectively), or a protein (peptide or polypeptide) the sequence of which consists of, or comprises, one or more copies of CDR 1, 2, or 3 (corresponding to SEQ ID NO:8, 9 or 10, respectively). In a specific embodiment, such a protein can be N or C-terminal modified, e.g., by C-terminal amidation or N-terminal acetylation.

In addition, techniques developed for the production of "chimeric antibodies" (Morrison, et al., 1984, Proc. Natl. Acad. Sci., 81, 6851-6855; Neuberger, et al., 1984, Nature 312, 604-608; Takeda, et al., 1985, Nature 314, 452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 5,816,397.) In a specific embodiment, the chimeric antibody comprises a variable domain of monoclonal antibody S2C6 secreted by the hybridoma as deposited with the ATCC and assigned accession number PTA-110, and a human constant region. In specific embodiments the variable domain of the chimeric antibody comprises the S2C6 $V_L$ (SEQ ID NO:2) as depicted in FIG. 3A and/or the S2C6 $V_H$ (SEQ ID NO:7) as depicted in FIG. 3B.

In addition, techniques have been developed for the production of humanized antibodies. (See, e.g., Queen, U.S. Pat. No. 5,585,089 and Winter, U.S. Pat. No. 5,225,539.) An immunoglobulin light or heavy chain variable region consists of a "framework" region interrupted by three hypervariable regions, referred to as complementarity-determining regions (CDRs). The extent of the framework region and CDRs have been precisely defined (see, "Sequences of Proteins of Immunological Interest", Kabat, E. et al., U.S. Department of Health and Human Services (1983). Briefly, humanized antibodies are antibody molecules from non-human species having one or more CDRs from the non-human species and framework regions from a human immunoglobulin molecule.

The invention encompasses an antibody or derivative thereof comprising a heavy or light chain variable domain, said variable domain comprising (a) a set of three complementarity-determining regions (CDRs), in which said set of CDRs are from monoclonal antibody S2C6, and (b) a set of four framework regions, in which said set of framework regions differs from the set of framework regions in monoclonal antibody S2C6, and in which said antibody or derivative thereof immunospecifically binds CD40. Preferably, the set of framework regions is from a human monoclonal antibody, e.g., a human monoclonal antibody that does not bind CD40.

In a specific embodiment, the invention encompasses an antibody or derivative thereof comprising a light chain variable domain, said variable domain comprising (a) a set of three complementarity-determining regions (CDRs), in which said set of CDRs comprises SEQ ID NO:3 or SEQ ID NO:4, and (b) a set of four framework regions, in which said set of framework regions differs from the set of framework regions in the light chain of monoclonal antibody S2C6, and in which said antibody or derivative thereof immunospecifically binds CD40.

In a specific embodiment, the invention encompasses an antibody or derivative thereof comprising a heavy chain variable domain, said variable domain comprising (a) a set of three complementarity-determining regions (CDRs), in which said set of CDRs comprises SEQ ID NO:8, SEQ ID NO:9, or SEQ ID NO:10, and (b) a set of four framework regions, in which said set of framework regions differs from the set of framework regions in the heavy chain of monoclonal antibody S2C6, and in which said antibody or derivative thereof immunospecifically binds CD40.

Alternatively, techniques described for the production of single chain antibodies (U.S. Pat. No. 4,946,778; Bird, 1988, Science 242, 423-426; Huston, et al., 1988, Proc. Natl. Acad. Sci. USA 85, 5879-5883; and Ward, et al., 1989, Nature 334, 544-546) can be adapted to produce single chain antibodies using S2C6 sequences. Single chain antibodies are formed by linking the heavy and light chain fragments of the Fv region via an amino acid bridge, resulting in a single chain polypeptide. In a specific embodiment, the single chain antibody comprises the amino acid sequences as depicted in FIGS. 3A and 3B (SEQ ID NOS:2 and 7, respectively).

In a specific embodiment, the antibody to a CD40 polypeptide, peptide or other derivative, or analog thereof comprising all or a portion of SEQ ID NO:1 or SEQ ID NO:6 is a bispecific antibody (see generally, e.g. Fanger and Drakeman, 1995, Drug News and Perspectives 8: 133-137). Such a bispecific antibody is genetically engineered to recognize both (1) an epitope and (2) one of a variety of "trigger" molecules, e.g. Fc receptors on myeloid cells, and CD3 and CD2 on T cells, that have been identified as being able to cause a cytotoxic T-cell to destroy a particular target. Such bispecific antibodies can be prepared either by chemical conjugation, hybridoma, or recombinant molecular biology techniques known to the skilled artisan. In a specific embodiment, the bispecific antibody contains a molecule comprising the S2C6 heavy or light chain variable domain or a CDR sequence thereof, which molecule has the structure of an antibody heavy or light chain but which differs from the native S2C6 heavy or light chain (e.g., by having amino acid substitution(s) in the framework region or a human constant domain).

Antibody fragments that retain the ability to recognize CD40 may be generated by known techniques. For example, such fragments include but are not limited to: The $F(ab')_2$ fragments, which can be produced by pepsin digestion of the antibody molecule and the F(ab') fragments, which can be generated by reducing the disulfide bridges of the $F(ab')_2$ fragments. Alternatively, Fab expression libraries may be constructed (Huse, et al., 1989, Science 246, 1275-1281) to allow rapid and easy identification of monoclonal Fab fragments with the desired specificity.

5.7 S2C6 Proteins, Derivatives and Analogs

In addition to those antibody molecules/variants described in Section 5.6 above, the invention further relates to S2C6 proteins, derivatives (including but not limited to fragments), analogs, and molecules of S2C6 proteins. Nucleic acids encoding S2C6 protein derivatives and protein analogs are also provided. In one embodiment, the S2C6 proteins are encoded by the nucleic acids described in Section 5.1 above. In particular aspects, the proteins, derivatives, or analogs are encoded by the sequence of SEQ ID NO:1 or SEQ ID NO:6.

The production and use of derivatives and analogs related to an S2C6 protein are within the scope of the present invention. In a specific embodiment, the derivative or analog is functionally active, i.e., capable of exhibiting one or more functional activities associated with a full-length, S2C6 protein. As one example, such derivatives or analogs which have the desired binding specificity can be used in immunoassays, or therapeutically for inhibition of tumor growth, etc. A specific embodiment relates to an S2C6 protein fragment that binds CD40 and potentiates binding of CD40L to CD40. Derivatives or analogs of an S2C6 protein can be tested for the desired activity by various immunoassays known in the art, including but not limited to competitive and non-competitive assay systems, using techniques such as radioimmunoassays, enzyme linked immunosorbent assay (ELISA), "sandwich" immunoassays, Western blots, immunofluorescence assays, protein A assays, immunoelectrophoretic assays, etc.

In addition, assays known in the art can be used to detect or measure the ability to inhibit cell proliferation (e.g., inhibition of tumor cell growth) or ability to stimulate cell proliferation (e.g., proliferation of B cells) in vivo or in vitro.

In particular, S2C6 derivatives can be made by altering S2C6 sequences by substitutions, additions (e.g., insertions) or deletions that provide for functionally equivalent molecules. Due to the degeneracy of nucleotide coding sequences, other DNA sequences which encode substantially the same amino acid sequence as an S2C6 gene may be used in the practice of the present invention. These include but are not limited to nucleotide sequences comprising all or portions of an S2C6 gene which is altered by the substitution of different codons that encode a functionally equivalent amino acid residue within the sequence, thus producing a silent change. Likewise, the S2C6 derivatives of the invention include, but are not limited to, those containing, as a primary amino acid sequence, all or part of the amino acid sequence of an S2C6 protein including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are generally understood to be conservative substitutions.

In a specific embodiment of the invention, proteins consisting of or comprising a fragment of an S2C6 protein consisting of at least 10 (continuous) amino acids of the S2C6 protein is provided. In other embodiments, the fragment consists of at least 20 or at least 50 amino acids of the S2C6 protein. In specific embodiments, such fragments are not larger than 50, 75, 100, or 200 amino acids. Derivatives or analogs of S2C6 proteins include but are not limited to those molecules comprising regions that are substantially homologous to an S2C6 protein or fragment thereof (e.g., in various embodiments, at least 60% or 70% or 80% or 90% or 95% identity over an amino acid sequence of identical size with no insertions or deletions or when compared to an aligned sequence in which the alignment is done by a computer homology program known in the art) or whose encoding nucleic acid is capable of hybridizing to a coding S2C6 gene sequence, under high stringency, moderate stringency, or low stringency conditions.

Specifically, by way of example computer programs for determining homology may include but are not limited to TBLASTN, BLASTP, FASTA, TEASTA, and CLUSTALW (Pearson and Lipman, 1988, Proc. Natl. Acad. Sci. USA 85(8):2444-8; Altschul et al., 1990, J. Mol. Biol. 215(3):403-10; Thompson, et al., 1994, Nucleic Acids Res. 22(22):4673-80; Higgins, et al., 1996, Methods Enzymol 266:383-402; Altschul, et al., 1990, J. Mol. Biol. 215(3):403-10). Default parameters for each of these computer programs are well known and can be utilized.

Specifically, Basic Alignment Search Tool (BLAST) (Altschul et al., 1990, J. of Molec. Biol., 215:403-410, "The BLAST Algorithm; Altschul et al., 1997, Nuc. Acids Res. 25:3389-3402) is a heuristic search algorithm tailored to searching for sequence similarity which ascribes significance using the statistical methods of Karlin and Altschul 1990, Proc. Natl. Acad. Sci. USA, 87:2264-68; 1993, Proc. Nat'l. Acad. Sci. USA 90: 5873-77. Five specific BLAST programs perform the following tasks: 1) the BLASTP program compares an amino acid query sequence against a protein sequence database; 2) the BLASTN program compares a nucleotide query sequence against a nucleotide sequence database; 3) the BLASTX program compares the six-frame conceptual translation products of a nucleotide query sequence (both strands) against a protein sequence database; 4) the TBLASTN program compares a protein query sequence against a nucleotide sequence database translated in al six reading frames (both strands); 5) the TBLASTX program compares the six-frame translations of a nucleotide query sequence against the six-frame translations of a nucleotide sequence database.

Smith-Waterman (database: European Bioinformatics Institute) (Smith-Waterman, 1981, J. of Molec. Biol., 147: 195-197) is a mathematically rigorous algorithm for sequence alignments.

FASTA (see Pearson et al., 1988, Proc. Nat'l. Acad. Sci. USA, 85:2444-2448) is a heuristic approximation to the Smith-Waterman algorithm. For a general discussion of the procedure and benefits of the BLAST, Smith-Waterman and FASTA algorithms see Nicolas et al., 1998, "A Tutorial on Searching Sequence Databases and Sequence Scoring Methods" and references cited therein.

The S2C6 derivatives and analogs of the invention can be produced by various methods known in the art. The manipulations which result in their production can occur at the gene or protein level. For example, a cloned S2C6 gene sequence can be modified by any of numerous strategies known in the art (Sambrook et al., 1989, Molecular Cloning, A Laboratory Manual, 2d ed., Cold Spring Harbor Laboratory Press, Cold Spring Harbor, N.Y.). The sequence can be cleaved at appropriate sites with restriction endonuclease(s), followed by further enzymatic modification if desired, isolated, and ligated in vitro. In the production of a modified gene encoding a derivative or analog of the S2C6 protein, care should be taken to ensure that the modified gene remains within the same translational reading frame as the native protein, uninterrupted by translational stop signals, in the gene region where the desired S2C6 protein activity is encoded.

Additionally, an S2C6 nucleic acid sequence can be mutated in vitro or in vivo, to create and/or destroy translation, initiation, and/or termination sequences, or to create variations in coding regions and/or to form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson et al., 1978, J. Biol. Chem. 253:6551), PCR with primers containing a mutation, etc.

Manipulations of an S2C6 protein sequence may also be made at the protein level. Included within the scope of the invention are S2C6 protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$, acetylation, formulation, oxidation, reduction, metabolic synthesis in the presence of tunicamycin, etc.

In addition, analogs and derivatives of an S2C6 protein can be chemically synthesized. For example, a peptide corresponding to a portion of an S2C6 protein which comprises the desired domain, or which mediates the desired activity in vitro, can be synthesized by use of a peptide synthesizer. Furthermore, if desired, nonclassical amino acids or chemical amino acid analogs can be introduced as a substitution or addition into the S2C6 sequence. Non-classical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, tbutylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In other specific embodiments, the S2C6 protein, fragment, analog, or derivative may be expressed as a fusion, or chimeric protein product (comprising the protein, fragment, analog, or derivative joined via a peptide bond to a heterologous protein sequence of a different protein). The heterologous protein sequence can comprise a biological response modifier, including but not limited to interferon-α, interferon γ, interleukin-2, interleukin-4, interleukin-6, and tumor necrosis factor, or a functionally active portion thereof. Alternatively, the heterologous protein sequence can comprise enzymes such as β-lactamase or carboxylesterases or toxins such as bryodin 1, *Pseudomonas* exotoxin A, or gelonin, or a functionally active portion thereof. Additionally, the S2C6 protein can be chemically linked to chemotherapeutic agents, including but not limited to alkylating agents (e.g. nitrogen mustards, nitrosoureas, triazenes); antimetabolites (e.g. folic acid analogs, pyrimidine analogs, purine analogs); natural products (e.g. antibiotics, enzymes, biological response modifiers); miscellaneous agents (e.g. substituted urea, platinum coordination complexes); and hormones and antagonists (e.g. estrogens, androgens, antiandrogen, gonadotropin releasing hormone analog); or functionally active portion thereof (see, e.g., Goodman and Gilman, The Pharmacological Basis of Therapeutics, Ninth Edition, McGraw-Hill, pp. 1225-1287, 1996). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. In different embodiments, the heterologous protein sequence can be covalently bound to the S2C6-related sequences by other than a peptide bond, e.g., by use of chemical crosslinking agents well known in the art.

In a specific embodiment, an S2C6 protein derivative is a chimeric or fusion protein comprising an S2C6 protein or fragment thereof (preferably consisting of at least a domain or motif of the S2C6 protein, or at least 10, 50 or 100 amino acids of the S2C6 protein) joined at its amino- or carboxy-terminus via a peptide bond to an amino acid sequence of a different protein. In a specific embodiment, the different protein is a toxin, enzyme or biological response modifier.

In specific embodiments, the amino acid sequence of the different protein is at least 6, 10, 20 or 30 continuous amino acids of the different protein or a portion of the different protein that is functionally active. In one embodiment, such a chimeric protein is produced by recombinant expression of a nucleic acid encoding the protein (comprising an S2C6-coding sequence joined in-frame to a coding sequence for a different protein). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Chimeric genes comprising portions of an S2C6 gene fused to any heterologous protein-encoding sequences may be constructed. A specific embodiment relates to a chimeric protein comprising a fragment of an S2C6 protein of at least 6 or 15 or 50 amino acids, or a fragment that displays one or more functional activities of the S2C6 protein (e.g., comprising copies of one or more CDRs).

In a specific embodiment, the S2C6 protein or derivative thereof is chemically linked to a chemotherapeutic drug including but not limited to doxorubicin, paclitaxel or docetaxel. Such a S2C6-drug conjugate can deliver the drug to cells expressing CD40. One or more drug molecules can be linked to the S2C6 protein or derivative. Linkages include but are not limited to hydrazone, peptide or carbohydrate linkages.

In another specific embodiment, the derivative is a molecule comprising a region of homology with an S2C6 protein. By way of example, in various embodiments, a first protein region can be considered "homologous" to a second protein region when the amino acid sequence of the first region is at least 30%, 40%, 50%, 60%, 70%, 75%, 80%, 90%, or 95% identical, when compared to any sequence in the second region of an equal number of amino acids as the number contained in the first region (without any insertions or deletions) or when compared to an aligned sequence of the second region that has been aligned by a computer homology program known in the art.

5.8 Hybridization Conditions

In a specific embodiment, a nucleic acid which is hybridizable to an S2C6 nucleic acid (e.g., having a sequence as set forth in SEQ ID NOS: 1 or 6), or to its reverse complement, or to a nucleic acid encoding an S2C6 derivative, or to its reverse complement under conditions of low stringency is provided. By way of example and not limitation, procedures using such conditions of low stringency are as follows (see also Shilo and Weinberg, 1981, Proc. Natl. Acad. Sci. U.S.A. 78, 6789-6792). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$p-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and re-exposed to film. Other conditions of low stringency which may be used are well known in the art (e.g., as employed for cross-species hybridizations).

In a specific embodiment, a nucleic acid which is hybridizable to an S2C6 nucleic acid (e.g., having a sequence as set forth in SEQ ID NOS: 1 or 6), or to its reverse complement, or to a nucleic acid encoding an S2C6 derivative, or to its reverse complement under conditions of high stringency is provided. By way of example and not limitation, procedures using such conditions of high stringency are as follows. Prehybridization of filters containing DNA is carried out for 8 h to overnight at 65° C. in buffer composed of 6.times.SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and $5-20 \times 10^6$ cpm of $^{32}$p-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

In a specific embodiment, a nucleic acid which is hybridizable to an S2C6 nucleic acid (e.g., having a sequence as set forth in SEQ ID NOS: 1 or 6), or to its reverse complement, or to a nucleic acid encoding an S2C6 derivative, or to its reverse complement under conditions of moderate stringency is provided. Selection of appropriate conditions for such stringencies is well known in the art (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, 1987-1997 Current Protocols,© 1994-1997 John Wiley and Sons, Inc.).

5.9 Therapeutic Uses

The invention provides for treatment or prevention of various diseases or disorders by administration of a therapeutic compound (termed herein "Therapeutic"). Such Therapeutics include but are not limited to: S2C6 antibodies and derivatives thereof (e.g., as described hereinabove); and nucleic acids encoding such S2C6 antibodies and derivatives (e.g., as described hereinabove). "Treatment" as used herein shall be deemed to include any clinically desirable or beneficial effect on the disease or disorder, including but not limited to alleviation of one or more symptoms, regression, slowing or cessation of progression, etc.

In specific embodiments of the invention, the Therapeutic is administered alone or in combination with CD40L for the treatment or prevention of malignancies (including but not limited to carcinoma and hematologic malignancies), inflammatory diseases, and disorders of the immune system. The Therapeutic and CD40L can, but need not be, contained within the same formulation, i.e., administration of the Therapeutic and CD40 can be performed separately but concurrently or during the same course of treatment. In a specific embodiment, the malignant cells express CD40. Alternatively, the cells of the malignancy need not express CD40, since endothelial cells of the vasculature associated with a malignant tumor should express CD40 and thus the Therapeutic of the invention should provide treatment efficacy even for tumors that do not express CD40. In a preferred embodiment, the Therapeutic potentiates the binding of CD40L to CD40 by at least 45%, 50%, 60%, or 65%.

In specific embodiments, the Therapeutic is used to increase the immune response of an immunosuppressed individual, such as a person suffering from acquired immunodeficiency syndrome, from malignancy, or an infant or elderly person.

In other embodiments of the invention, the Therapeutic may be chemically modified so that cells that it binds to are killed. Such cells include but are not limited to multiple myeloma cells, lymphoma cells or carcinomas. Since all B-cells express CD40, this approach can result in suppression of the immune response. For example, a cytotoxic drug linked to S2C6 sequences (e.g., a fusion protein) may be used in vivo to cause immunosuppression in order to cross histocompatibility barriers in transplant patients; alternatively, these modified ligands may be used to control autoimmune diseases.

In other embodiments, the Therapeutic may be used to promote the proliferation and/or differentiation of CD40-bearing cells that are not B cells, for example, lung carcinoma cells, as a means of directly treating malignancy or as an adjunct to chemotherapy.

Malignancies which may be treated or prevented using a Therapeutic of the invention include but are not limited to those in Table 1:

TABLE 1

MALIGNANCIES AND RELATED DISORDERS

Leukemia
    acute leukemia
        acute lymphocytic leukemia
        acute myelocytic leukemia
            myeloblastic
            promyelocytic
            myelomonocytic
            monocytic
            erythroleukemia
    chronic leukemia
        chronic myelocytic (granulocytic) leukemia
        chronic lymphocytic leukemia
Polycythemia vera
Lymphoma
    Hodgkin's disease
    non-Hodgkin's disease
Multiple myeloma
Waldenstrom's macroglobulinemia
Heavy chain disease
Solid tumors
    sarcomas and carcinomas
        fibrosarcoma
        myxosarcoma
        liposarcoma
        chondrosarcoma
        osteogenic sarcoma
        osteosarcoma
        chordoma
        angiosarcoma
        endotheliosarcoma
        lymphangiosarcoma
        lymphangioendotheliosarcoma
        synovioma
        mesothelioma
        Ewing's tumor
        leiomyosarcoma
        rhabdomyosarcoma
        colon carcinoma
        colorectal carcinoma
        pancreatic cancer
        breast cancer
        ovarian cancer
        prostate cancer
        squamous cell carcinoma
        basal cell carcinoma
        adenocarcinoma
        sweat gland carcinoma
        sebaceous gland carcinoma
        papillary carcinoma TABLE 1-continued

MALIGNANCIES AND RELATED DISORDERS papillary adenocarcinomas
cystadenocarcinoma
medullary carcinoma
bronchogenic carcinoma
renal cell carcinoma
hepatoma
bile duct carcinoma
choriocarcinoma
seminoma
embryonal carcinoma
Wilms' tumor
cervical cancer
uterine cancer
testicular tumor
lung carcinoma
small cell lung carcinoma
non small cell lung carcinoma
bladder carcinoma
epithelial carcinoma
glioma
astrocytoma
medulloblastoma
craniopharyngioma
ependymoma
pinealoma
hemangioblastoma
acoustic neuroma
oligodendroglioma
menangioma
melanoma
neuroblastoma
retinoblastoma
nasopharyngeal carcinoma
esophageal carcinoma Inflammatory diseases and deficiencies or disorders of the immune system which may be treated or prevented using a Therapeutic of the invention include but are not limited to those in Table 2:

TABLE 2

INFLAMMATORY DISEASES AND IMMUNE SYSTEM DISORDERS systemic lupus erythematosus (SLE)
Scleroderma (e.g., CRST syndrome)
inflammatory myositis
Sjogren's syndrome (SS)
mixed connective tissue disease (e.g., MCTD, Sharp's syndrome)
rheumatoid arthritis
multiple sclerosis
inflammatory bowel disease (e.g., ulcerative colitis, Crohn's disease)
acute respiratory distress syndrome
pulmonary inflammation
osteoporosis
delayed type hypersensitivity
asthma
primary biliary cirrhosis (PBC)
idiopathic thrombocytopenic purpura (ITP)

5.9.1 Effective Dose

Toxicity and therapeutic efficacy of such Therapeutics can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapeutics that exhibit large therapeutic indices are preferred. While Therapeutics that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. Exemplary doses include but are not limited to from 1 ng/kg to 100 mg/kg. The dosage of such Therapeutics lies preferably within a range of circulating concentrations that include the $ED_{50}$ with little or no toxicity. The dosage may vary within this range depending upon the dosage form employed and the route of administration utilized. For a Therapeutic, the therapeutically effective dose may preferably be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

5.9.2 Formulations

Pharmaceutical compositions for use in accordance with the present invention may be formulated in conventional manner using one or more physiologically acceptable carriers or excipients.

Thus, the Therapeutics and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate) lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicles before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the Therapeutics for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Capsules and cartridges of, e.g., gelatin for use in an inhaler or insufflator may be formulated containing a powder mix of the compound and a suitable powder base such as lactose or starch.

The Therapeutics may be formulated for parenteral administration by injection, e.g., by bolus injection or continuous infusion. Formulations for injection may be presented in unit dosage form, e.g., in ampoules or in multi-dose containers, with or without an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The Therapeutics may also be formulated in rectal compositions such as suppositories or retention enemas, e.g., containing conventional suppository bases such as cocoa butter or other glycerides.

In addition to the formulations described previously, the Therapeutics may also be formulated as a depot preparation. Such long acting formulations may be administered by implantation (for example subcutaneously or intramuscularly) or by intramuscular injection. Thus, for example, the Therapeutics may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration preferably for administration to a human.

In specific embodiments, the invention provides a pharmaceutical composition comprising a therapeutically effective amount of a Therapeutic in combination with CD40 ligand.

The invention is further described in the following examples which are in no way intended to limit the scope of the invention.

6. EXAMPLE

Cloning of SC26 Variable Regions 6.1 Materials and Methods

The S2C6 light chain and heavy chain variable regions were cloned using methods essentially as described in Gilliland et al., 1996, Tissue Antigens 47:1-20. Total RNA was isolated from the S2C6 hybridoma. First strand complementary DNA (cDNA) was prepared for the mouse kappa light chain and heavy chain variable regions using reverse transcriptase and anti-sense primers that annealed approximately 100 base pairs downstream of the JC junction. A poly-G tail was added to the cDNA strands using terminal transferase and then double stranded DNA was synthesized using the polymerase chain reaction (PCR). The PCR primers, specific for the poly-G tail or a sequence approximately 50 bases inside the cDNA for the light chain or heavy chain, were designed to include unique restriction sites. After amplification, the PCR products were digested with EcoRI and HindIII cloned into pUC19 that had been digested with the same restriction enzymes. These reactions were ligated, transformed into *E. coli* DH5α, and the resulting clones were screened by restriction analysis. Clones that were positive by restriction digestion analysis were sequenced by DNA sequencing on a Li-Cor fluorescence sequencer. The nucleotide (SEQ ID NO:1) and amino acid (SEQ ID NO:2) sequences of the light chain variable region ($V_L$) are shown in FIG. 1. The nucleotide (SEQ ID NO:6) and amino acid (SEQ ID NO:7) sequences of the heavy chain variable region ($V_H$) are shown in FIG. 2. FIGS. 3A-3B illustrate the amino acid sequence of S2C6 $V_L$ and S2C6 $V_H$ (FIGS. 3A and 3B, respectively). The CDRs are underlined. The amino acid sequences of V.sub.L CDRs 1-3 correspond to SEQ ID NOS:3-5, respectively. The amino acid sequences of $V_H$ CDRs 1-3 correspond to SEQ ID NOS:8-10, respectively.

The resulting DNA sequences were then compared to the light chain and heavy chain variable regions of other murine antibodies of the same isotype and the reading frame and corresponding amino acid sequences for the genes isolated from S2C6 were determined. To confirm the amino acid sequences, the light chain and heavy chain variable regions of S2C6 mAb were subjected to N-terminal amino acid analysis.

The amino acid sequences of S2C6 VL, S2C6 VH and the CDRs of both the VL and VH were submitted for BLASTP searches on Apr. 21, 1999 using both the NR database (All non-redundant GenBank CDS translations+PDS+SwissProt+PIR+PRF) and the Kabat database (Kabat's database of sequences of immunological interest). The sequences found using the NR database can be retrieved using the Accession number. The sequences found using the Kabat database can be retrieved using the Accession number and SEQHUNTII. The results of these searches are shown below:

BLASTP Searches Using NR Database

S2C6 VL (SEQ ID NO:2): a BLASTP search of the NR database with S2C6 VL as the query yielded no hits with 100% identity and 6 hits with 94% (106/112) identity. These 6 are shown below:

pir||PT0359 IgG kappa chain V region (R4A. 12)—mouse (fragment)

gi|196660 (M59949) immunoglobulin kappa-chain VJ region [*Mus musculus*]

gi|196954 (M12183) kappa-chain V-region [*Mus musculus*]>gi|2247 *[Mus musculus]* pir||B34904 Ig kappa chain precursor V region (12-40 and 5-14) . . .

emb|CAA80076| (Z22102) immunoglobulin variable region [*Mus musculus*]

dbj|BAA22172|| (AB006833) anti-pseudouridine monoclonal antibody . . .

VL CDR1 (SEQ ID NO:3): a BLASTP search with VL CDR1 as the query yielded no hits with 100% identity and numerous hits with 93% identity (15/16). The first 5 of these are shown below:

dbj|BAA03480| (D14627) immunoglobulin gamma-3 kappa chain [*Mus musculus*]

dbj|BAA22172| (AB006833) anti-pseudouridine monoclonal antibody . . .

gi|4101647 (AF005352) immunoglobulin V-region light chain [*Mus musculus*]

gi|3377681 (AF078800) single chain anti-HIV-1 Rev variable fragment . . .

gi|1870366 (U55625) anti-DNA immunoglobulin light chain IgM [*Mus musculus*]

VL CDR2 (SEQ ID NO:4): a BLASTP search of the NR database with VL CDR2 as the query yielded no hits.

VL CDR3 (SEQ ID NO:5): a BLASTP search of the NR database with VL CDR3 as the query yielded no hits.

S2C6 VH (SEQ ID NO:7): a BLASTP search of the NR database using S2C6 VH as a query yielded no hits with 100% identity and numerous hits with up to 88% identity the first 5 of which are shown below:

gi|3561044 (AF083186) anti-HIV-1 p24 antibody D2 heavy chain [*Mus musculus*]

pdb|1A6T|B Chain B, Fab Fragment Of Mab1-Ia Monoclonal Antibody gi|2895955 (AF045895) IgG1 heavy chain mAB1-IA [*Mus musculus*]

emb|CAA800231 (Z22049) immunoglobulin variable region [*Mus musculus*]

gi|194510 (M91695) immunoglobulin gamma-1 chain [*Mus musculus*]

VH CDR1 (SEQ ID NO:8): a BLASTP search of the NR database with VH CDR1 as the query yielded no hits.

VH CDR2 (SEQ ID NO:9): a BLASTP search of the NR database with VH CDR2 as the query yielded no hits with 100% identity, 1 hit with 94% identity (16/17) and numerous hits with less than 94% identity. The 1 hit with 94% identity is shown:

gi|3561044 (AF083186) anti-HIV-1 p24 antibody D2 heavy chain [*Mus musculus*]

VH CDR3 (SEQ ID NO:10): a BLASTP search of the NR database with VH CDR3 as the query yielded no hits.

Blast Searches Using Kabat Database

S2C6 VL (SEQ ID NO:2): a BLASTP search of the Kabat database using S2C6 VL as the query yielded no hits with 100% identity and numerous hits with 89-91% identity to the query. The first 5 are shown:

KADBID 005591, mouse IG KAPPA LIGHT CHAIN VARIABLE REGION (5-14 . . . ),

KADBID 005594, mouse IG KAPPA LIGHT CHAIN VARIABLE REGION (10VA . . . ),

KADBID 005593, mouse IG KAPPA LIGHT CHAIN VARIABLE REGION (12-4 . . . ),

KADBID 005603, mouse IG KAPPA LIGHT CHAIN VARIABLE REGION (17 s . . . ),

KADBID 005588, mouse IG KAPPA LIGHT CHAIN VARIABLE REGION (TEPC . . . ).

VL CDR1 (SEQ ID NO:3): a BLASTP search of the Kabat database with VL CDR1 as the query yielded no hits with 100% identity and numerous hits with 93% identity (15/16). The first 5 are shown below:

KADBID 005720, mouse IG KAPPA LIGHT CHAIN VARIABLE REGION (BW24 . . . ),

KADBID 005614, mouse IG KAPPA LIGHT CHAIN VARIABLE REGION (PME7 . . . ),

KADBID 005624, mouse IG KAPPA LIGHT CHAIN VARIABLE REGION (C5-7 . . . ),

KADBID 005621, mouse IG KAPPA LIGHT CHAIN VARIABLE REGION (40-6 . . . ),

KADBID 005640, mouse IG KAPPA LIGHT CHAIN VARIABLE REGION (40-9 . . . ).

VL CDR2 (SEQ ID NO:4): a BLASTP search of the Kabat database with VL CDR2 as the query yielded no hits.

VL CDR3 (SEQ ID NO:5): a BLASTP search of the Kabat database with VL CDR3 as the query yielded 1 hit with 100% identity to the query:

KADBID 005681, mouse IG KAPPA LIGHT CHAIN VARIABLE REGION(NC 10 . . . ).

S2C6 VH (SEQ ID NO:7): a BLASTP search of the Kabat database using S2C6 VH as the query yielded no hits with 100% identity and numerous hits with 79-85% identity to the query. The first 5 of the hits are shown below:

KADBID 001498, mouse IG HEAVY CHAIN VARIABLE REGION (HDEX24),

KADBID 001494, mouse IG HEAVY CHAIN VARIABLE REGION (HDEX5),

KADBID 001529, mouse IG HEAVY CHAIN VARIABLE REGION (163.72'CL),

KADBID 001500, mouse IG HEAVY CHAIN VARIABLE REGION(HDEX37),

KADBID 001597, mouse IG HEAVY CHAIN VARIABLE REGION (BB128'CL),

VH CDR1 (SEQ ID NO:8): a BLASTP search of the Kabat database with VH CDR1 as the query yielded no hits VH CDR2 (SEQ ID NO:9): a BLASTP search of the Kabat database with VH CDR as the query yielded no hits with 100% identity and 10 hits with 87-88% identity to the query. The first 5 are shown:

KADBID 001535, mouse IG HEAVY CHAIN VARIABLE REGION (H10"CL),

KADBID 001534, mouse IG HEAVY CHAIN VARIABLE REGION(H81'CL),

KADBID 001533, mouse IG HEAVY CHAIN VARIABLE REGION(H50'CL),

KADBID 019741, mouse IG HEAVY CHAIN VARIABLE REGION (Clone F'CL),

KADBID 001529, mouse IG HEAVY CHAIN VARIABLE REGION (163.72'CL),

VH CDR3 (SEQ ID NO:10): BLASTP search of the Kabat database with VH CDR3 as the query yielded no hits.

7. EXAMPLE

Biologic Activity of S2C6

7.1 Materials and Methods 7.1.1 Anti-CD40 Antibody Preparation

The S2C6 hybridoma was cultured at 37° C. in complete IMDM (Gibco BRL, Grand Island, N.Y.) containing 10% fetal bovine serum (FBS), 100 units/ml penicillin and 100 mg/ml streptomycin. The culture was harvested by centrifugation and the supernatant was collected by filtration using a 0.2 micron filter. Subsequently the supernatant was loaded onto a GammaBind™ Sepharose column (Pierce), washed with phosphate buffered saline (PBS), and eluted with 0.1 M glycine pH 2.5. Immediately upon elution, the antibody was neutralized with 1 M Tris pH 8.0, dialyzed into PBS, and filter sterilized. MAb preparations were analyzed by size exclusion chromatography. Only samples of greater than 99% monomeric protein were used for the studies described herein.

7.1.2 Human Tumor Xenograft Models

Ninety female C.B.-17 SCID mice were obtained (Taconic Labs, Germantown, N.Y.) at age 6 to 8 weeks and quarantined for 2 weeks. Control groups of mice were injected intravenously (i.v.) with a human B cell tumor line: Ramos (non-Hodgkins lymphoma), HS Sultan (multiple myeloma) or IM-9 (multiple myeloma) cells ($1\times10^6$–$2\times10^6$ cells). The remaining mice were divided into two groups; half were treated with 200. µl of a 1:10 dilution of anti-asialo-GM1 (Wako Chemicals, Richmond, Va.) i.v., one day prior to the injection of tumor cells, to remove host natural killer cells (Murphy et al., 1992, Eur. J. Immunol. 22:241). Mice in the two groups were injected i.v. with Ramos, HS Sultan or IM-9 cells ($1\times10^6$–$2\times10^6$ cells). Mice in the test groups were then injected intraperitoneally (i.p.) with 1 mg/kg of S2C6 IgG prepared as described in Section 7.1.2 starting on day 1 or day 5 post tumor implant, according to the following schedule and were monitored for partial paralysis or other signs of disease.

| | | Xenograft Tumor Model Schedule | | |
|---|---|---|---|---|
| Group | Tumor cell lines | Antibody (1 mg/kg, i.p.) | Anti-asialo GM1 | Days treated with mAb |
| 1 Control | Ramos | — | − | — |
| 2 | Ramos | S2C6 | − | 1, 5, 9, 13, 17 |
| 3 | Ramos | S2C6 | − | 5, 9, 13, 17, 21 |
| 4 | Ramos | S2C6 | + | 1, 5, 9, 13, 17 |
| 5 | Ramos | S2C6 | + | 5, 9, 13, 17, 21 |
| 6 Control | HS Sultan | — | − | — |
| 7 | HS Sultan | S2C6 | − | 1, 5, 9, 13, 17 |
| 8 | HS Sultan | S2C6 | − | 5, 9, 13, 17, 21 |
| 9 | HS Sultan | S2C6 | + | 1, 5, 9, 13, 17 |
| 10 | HS Sultan | S2C6 | + | 5, 9, 13, 17, 21 |
| 11 Control | IM-9 | — | − | — |
| 12 | IM-9 | S2C6 | − | 1, 5, 9, 13, 17 |
| 13 | IM-9 | S2C6 | − | 5, 9, 13, 17, 21 |
| 14 | IM-9 | S2C6 | + | 1, 5, 9, 13, 17 |
| 15 | IM-9 | S2C6 | + | 5, 9, 13, 17, 21 |

7.1.3 Peripheral Blood B Cell Isolation

Peripheral blood B cells were isolated by positive selection using immobilized antibodies against both CD19 and CD20. The final isolated cell population contained greater than 85% B cells as determined by flow cytometry. For storage, the cells were diluted to $4 \times 10^7$ cells/ml in fetal bovine serum (FBS) containing 10% dimethyl sulfoxide and stored in a liquid nitrogen freezer.

7.1.4 B Cell Proliferation Assay

Human peripheral blood B cells were thawed and incubated in 96-well tissue culture plates at $1 \times 10^5$ per well in IMDM medium plus 10% FBS in the presence of 5 ng/ml recombinant human IL-4 (Biosource) and various dilutions of an anti-CD40 mab: S2C6, G28-5 (Bristol-Myers Squibb) or M3 (Genzyme #80-3702-04). As a control, cells were incubated with IL-4 and an irrelevant control mAb, EXA2-1H8 (anti-Pseudomonas exotoxin). The plates were incubated at 37° C. for 3 days and then pulsed for 16 h with 0.5 mCi$^3$H-thymidine/well. Cells were harvested onto 96-well glass fiber filters using a Filtermate 196 Harvester™ (Packard Instruments) and combined with scintillation fluid. The extent of $^3$H-thymidine incorporated into nascent DNA was measured by liquid scintillation counting using a Topcount LSC™ (Packard Instruments).

A Jurkat cell line selected to express constitutive high levels of CD40L ("Jurkat/CD40L"), was used as CD40L stimulator cells (Malik et al., 1996, J. Immunol. 156:3952-60). To eliminate proliferation of the stimulator cells, they were treated with mitomycin C (50 mg/ml) in PBS for 20 min at 37° C. followed by 3 washes in PBS prior to combining with B cells. B cells ($1 \times 10^5$/well) were combined with Jurkat/CD40L cells and assayed as above. B cells and IL-4 were initially combined with stimulator cells ($2.5 \times 10^4$/well) directly followed by addition of the anti-CD40 mAbs. Monoclonal antibodies were titrated with either a fixed concentration of stimulator cells or stimulator cells were titrated with a fixed concentration of mAb.

7.1.5 CD40/CD40L Binding Assay

The Jurkat/CD40L cell line was used as a target cell line in these assays. Cells were adjusted toga density to $2 \times 10^7$/ml at 50µ per sample. Binding was performed in RPMI 1640 media (Gibco)+10% FBS. To determine receptor saturation, Jurkat/CD40L cells were incubated with increasing concentrations of CD40-Ig (a soluble fusion protein of CD40 and human immunoglobulin) (Noelle et al., 1992, Proc. Natl. Acad. Sci. USA 89:6550-6554), washed and incubated with fluorescein isothiocyanate conjugated to anti-human immunoglobulin ("FITC-anti-human Ig"). The resultant binding was evaluated using a FacScan™ flow cytometer (Becton Dickinson). Recombinant soluble CD40-Ig (25 µg/ml) was pre-incubated for 1 h on ice with increasing concentrations of mAb S2C6. The anti-CD40 mAb G28-5; M3; and anti-*Pseudomonas* exotoxin, an isotype control, were used for comparison. The recombinant human soluble CD40 ligand (CD 154-muCD8), produced as a fusion protein with murine CDB and labeled with FITC, was obtained from Research Diagnostics, Inc. (Flanders, N.J.). Dilutions of soluble CD40-Ig and anti-CD40 mAbs were made at a 4-fold final concentration, pre-incubated on ice for 1 h and then combined with Jurkat cells on ice for 1 h. Cells were washed and labeled with FITC-Goat anti-human F(ab')$_2$, (Jackson Labs, Fc-specific #109-096-098). The extent of CD40 binding was determined by flow cytometry.

7.2 Results 7.2.1 In Vitro Studies: mAb S2C6 Promotes CD40/CD40L Interaction

To evaluate the effect of anti-CD40 mAbs on the binding of soluble CD40 to CD40L expressed on the surface of activated T cells, increasing concentrations of various CD40 mAbs were pre-incubated with 25 µg/ml soluble CD40-Ig followed by incubation of the complexes with Jurkat/CD40L cells. CD40L expression on selected CD40L$^+$ Jurkat T cells was initially verified by flow cytometry with FITC-labeled anti-CD40L (data not shown). CD40 binding to CD40L on these target cells was then determined by flow cytometry of the Jurkat/CD40L cells using FITC-goat anti-human Ig to detect the bound CD40-Ig. Titration with CD40-Ig showed receptor saturation at approximately 25 µg/ml CD40-Ig. Using saturating concentrations of soluble CD40, S2C6 complexed with CD40 at ratios ranging from 0.25 to 2:1 (mass:mass) resulted in a dose-dependent increase in CD40 binding to CD40L (approximately 50%, 100%, 146% and 220% at concentrations of approximately 6 µg/ml, 13 µg/ml, 25 µg/ml, and 50 µg/ml, respectively) (FIG. 4). A similar titration with the inhibitory antibody M3 blocked CD40/CD40L binding in a dose dependent manner. mAb G28-5 showed no effect of CD40/CD40L binding at concentrations up to 25 µg/ml and was only slightly stimulatory at the highest concentration tested (50 µg/ml), relative to control EXA2-1H81 g.

These data clearly indicate mAb S2C6 promotes CD40/CD40L interaction. Further, S2C6 differs from G28-5 and M3 in its ability to increase CD40/CD40L interaction.

In a reciprocal assay, the effect of anti-CD40 mAbs on the binding of soluble CD40L to membrane-bound CD40 expressed on the surface of B cells was evaluated. Titration with soluble CD40L showed Ramos B cell surface CD40 saturation at approximately 10 µg/ml. Increasing concentrations of various anti-CD40 mAbs were pre-incubated with CD40-expressing B cells followed by incubation of the cells with FITC-labeled soluble CD40L. The labeled CD40L binding to CD40 on target B cells was then determined by flow cytometry of the Ramos cells. Using saturating concentrations of soluble CD40L, mAb S2C6 complexed with CD40-expressing cells resulted in a maximal increase in CD40L binding of approximately 51% to 68% at concentrations ranging from 0.04 to 2 µg/ml (FIG. 5).

In contrast to the above results with soluble CD40, in which mAb G28-5 had little effect on CD40/CD40L interaction, G28-5 showed inhibition of soluble ligand binding to CD40 at all concentrations tested. A similar titration with the inhibitory mAb M3 also blocked CD40L/CD40 binding in a dose dependent manner.

These data indicate that S2C6 differs surprisingly from G28-5 and M3 in its ability to increase CD40L/CD40 interaction. Moreover, under these conditions, both mAb G28-5 and mAb M3 inhibit the interaction of soluble CD40L with CD40 at concentrations as low as 40 ng/ml.

7.2.2 In vitro Studies: mAb S2C6 Increases B Cell Response to CD40/CD40L

The growth response of primary peripheral B cells to CD40L-expressing cells was measured in the presence of an anti-CD40 mAb (S2C6, G28-5 or M3). First, B cells were combined with increasing numbers of non-proliferating, Jurkat/CD40L cells in the presence or absence of a fixed level (30 ng/ml) of the various mAbs. B cell activation in response to treatment was then measured by .sup.3H-thymidine incorporation at 72 h post-stimulus. T cell titration in the presence of mAb M3 resulted in B cell proliferation similar to that seen with control Ig (FIG. 6).

Although mAb G28-5 provided some B cell activation in the absence of ligand (FIG. 7), $CD40L^+$ T cell titration in the presence of G28-5 only nominally increased B cell proliferation (1.3-fold) over the level seen with G28-5 alone. In contrast, B cell proliferation increased in the presence of S2C6 in a dose dependent manner with increasing numbers of T cell stimulator cells to 3-fold above mAb-only stimulation with a B cell to T cell stimulator ratio of 4:1.

These data demonstrate that unlike M3 and G28-5, S2C6 can surprisingly synergize with CD40L to promote B cell proliferation via CD40.

In a second assay of this type, B cells were either titrated with an anti-CD40 mAb or combined with non-proliferating $CD40L^+$ T stimulator cells at a fixed ratio of 4:1 (B:T) and titrated with an anti-CD40 mAb (FIG. 7).

These results demonstrate that, under these conditions, activation of primary human peripheral blood B cells increased 2-fold at 10 μg/ml of mAb G28-5 and ligand, as compared to G28-5 alone. To a surprising degree, S2C6 was significantly more active and in the presence of ligand increased B cell proliferation in a dose dependent manner to 16.2-fold at 10 μg/ml (the highest level tested) as compared to S2C6 alone.

Taken together, these data indicate that S2C6 complexed to CD40 increases CD40L binding. Although S2C6 by itself will stimulate B cell proliferation in a manner similar to G28-5, S2C6 is distinguished from G28-5 by its ability to increase CD40L binding and the subsequent magnitude of the CD40L-mediated activation signal.

8. EXAMPLE

Monoclonal Antibody S2C6 Inhibits Tumor Growth

To evaluate the anti-tumor activity of native mAb S2C6, female C.B.-17 SCID mice were divided into two groups (20 mice/group). Half of the mice of each group were treated with anti-asialo-GM 1 to blunt host natural killer cell activity (Murphy et al., 1992, Eur. J. Immunol. 22:241). The following day, mice were injected i.v. with Ramos, HS Sultan or IM-9 cells ($1\times10^6$ cells). Mice were then injected i.p. with 1 mg/kg of mAb S2C6 IgG, as described in Materials and Methods in Section 7 supra and monitored for partial paralysis or other signs of disease onset.

Monoclonal antibody S2C6 treatment of animals harboring Ramos human B cell lymphoma (FIG. 8A), HS Sultan multiple myeloma (FIG. 8B), or IM-9 multiple myeloma (FIG. 8C), resulted in significant reduction in tumor mass and subsequent tumor-related morbidity and mortality. In parallel studies, efficacy was sustained in the presence of anti-asialo-GM 1, suggesting that the increased survival in the presence of mAb S2C6 was not due to nonspecific NK activity. The IM-9 cell line is an aggressive tumor model that, like multiple myeloma, secretes human Ig as a surrogate marker of disease.

Treatment of IM-9 diseased mice with mAb S2C6 significantly increased animal survival. These studies clearly demonstrate that S2C6 has potent anti-tumor activity against engrafted human tumors in mice.

9. EXAMPLE

A Single-Chain Anti-CD40 Immunotoxin Fusion Protein Binds CD40-IG

BD1-S2C6 sFv (single-chain anti-CD40 immunotoxin, a fusion protein consisting of the amino acid sequence of bryodin 1 (BD1) (Francisco et al., 1997, J. Biol. Chem. 272(39): 24165-24169) fused to the variable regions of monoclonal antibody S2C6) was expressed in *E. coli* as inclusion bodies, denatured and refolded.

Briefly, total RNA was isolated from S2C6 hybridoma cells using TRIZOL reagent (Life Technologies) following the manufacturer's recommendations. First strand cDNA synthesis of the light chain and heavy chain variable regions was performed essentially as described by Gilliland et al. (Tissue Antigens, 47:1-20 (1996)) using primers which are complementary to sequences approximately 100 bases downstream of the J-C junctions. The first strands were then poly-G tailed and amplified by PCR using a poly-C anchor primer, which is complementary to the poly-G tail, and a primer nested approximately 50 bases inside the one used for first strand synthesis. The PCR primers were designed to generate unique restriction sites at the 5' and 3' ends of the PCR products. The two PCR products, containing the sequences coding for the light chain and heavy chain variable regions, were digested with EcoRi and HINDIII and ligated into pUC19 which had been digested with the same enzymes. The resulting plasmids, pSG5 and pSG10, contain the DNA coding for S2C6 VL and S2C6 VH, respectively. The DNA of both plasmids was sequenced and verified to match the amino-terminal acid sequence of the parental monoclonal antibody.

The VH and VL fragments of S2C6 were "sewn" together (overlap extension PCR) as described by Gilliland et al. in the VH-VL orientation and ligated into a cloning vector. Subsequently the sFv fragment of BD1-G28-5 sFv (Francisco et al., 1997, J. Biol. Chem. 272:24165-24169) was removed from pSE151 by restriction digestion and S2C6 sFv was ligated in its place. The resulting plasmid, pSG40, contains the gene coding for BD1-S2C6 sFv under the control of the inducible T7 promoter.

For expression, pSG40 was transformed into competent *E. coli* strain BL21(DE3)pLysS cells and the cells were grown in T-broth at 37° C. When the culture reached $OD_{600}$=1.0 the cells were induced with 1 mM isopropyl-β-D-thiogalactopyranoside (IPTG) for 3 h. Subsequently, the cells were harvested by centrifugation, lysed by sonication, and the BD1-S2C6 sFv fusion was isolated as insoluble inclusion bodies by centrifugation, which were denatured and refolded as follows: Inclusion bodies were solubilized in 7M guanidine at 5 mg/ml, refolded by rapid dilution (1:100) into PBS containing 0.3M L-arginine and 2 mM DTT, and dialyzed against 20 mM sodium phosphate buffer, pH 7.4, for subsequent purification.

The refolded protein was isolated using Blue Sepharose followed by affinity chromatography over immobilized CD40-Ig.

The purified protein was then tested for binding to immobilized CD40-Ig in ELISA. Microtiter plates were coated with CD40-Ig at 0.5 µg/ml followed by the addition of dilutions of purified BD1-S2C6 sFv in PBS (pH 7.4) with 1% bovine serum albumin and 0.05% Tween-20 in the presence of 25 µg/ml S2C6 mAb (.tangle-solidup.), 25 µg/ml control antibody BR96 (●), or no excess antibody ( ). Binding of BD1-S2C6 sFv to the immobilized receptor was detected by the addition of BD1-specific rabbit antiserum (Seattle Genetics, Inc., Bothell, Wash.) followed by the addition of horseradish peroxidase conjugated goat anti-rabbit Ig.

The binding of BD1-S2C6 sFv to CD40-Ig was completely inhibited by the addition of excess S2C6 mAb but not by the addition of the control mAb (FIG. 9).

10. DEPOSIT OF HYBRIDOMA

Hybridoma S2C6, secreting native monoclonal antibody S2C6, was deposited on May 25, 1999, with the American Type Culture Collection (ATCC), 10801 University Boulevard, Manassass, Va. 20110-2209, under the provisions of the Budapest Treaty on the International Recognition of the Deposit of Microorganisms for the Purpose of Patent Procedures, and assigned accession number PTA-110.

11. SPECIFIC EMBODIMENTS, CITATION OF REFERENCES

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references, including patent applications, patents, and scientific publications, are cited herein, the disclosures of which are incorporated herein by reference in their entireties.

What is claimed is:

1. A method for treatment of cancer in a subject having a CD40-positive cancer, comprising administering to the subject a therapeutically effective amount of an unconjugated antibody, wherein the antibody:
   (i) immunospecifically binds CD40,
   (ii) increases the binding of CD40 ligand to cell surface CD40 by at least 45%, and
   (iii) is a chimeric or humanized form, or fragment thereof, of monoclonal antibody S2C6 as secreted by the hybridoma deposited with the ATCC and assigned accession number PTA-110.

2. The method of claim 1, wherein the antibody is a single-chain antibody or a scFv.

3. The method of claim 1, wherein the antibody is a chimeric antibody.

4. The method of claim 3, wherein the chimeric antibody comprises light and heavy chain variable regions having the amino acid sequences of SEQ ID NO:2 and SEQ ID NO:7, respectively.

5. The method of claim 3, wherein the antibody comprises a human variable region framework region.

6. The method of claim 1, wherein the antibody is a humanized antibody.

7. The method of claim 1, wherein the cancer is a hematologic malignancy.

8. The method of claim 7, wherein the hematologic malignancy is a lymphoma.

9. The method of claim 8, wherein the lymphoma is Hodgkin's lymphoma.

10. The method of claim 8, wherein the lymphoma is non-Hodgkin's lymphoma.

11. The method of claim 7, wherein the hematologic malignancy is multiple myeloma.

12. The method of claim 7, wherein the hematologic malignancy is a chronic leukemia.

13. The method of claim 12, wherein the chronic leukemia is chronic myelocytic leukemia or chronic lymphocytic leukemia.

14. The method of claim 1, wherein the cancer is a carcinoma.

15. The method of claim 14, wherein the carcinoma is an ovarian, lung or bladder carcinoma.

16. The method of claim 1, wherein the binding of soluble CD40 ligand to CD40 on the surface of Ramos B cells is increased in vitro by at least 50%, when the soluble CD40 ligand is present at a concentration that results in saturation of binding of the soluble CD40 ligand to Ramos B cell surface CD40.

17. The method of claim 16, wherein the antibody is present at a concentration of 0.04 to 2 µg/ml.

* * * * *